US008557562B2

(12) United States Patent
Bramucci et al.

(10) Patent No.: US 8,557,562 B2
(45) Date of Patent: Oct. 15, 2013

(54) YEAST WITH INCREASED BUTANOL TOLERANCE INVOLVING FILAMENTOUS GROWTH RESPONSE

(75) Inventors: Michael G. Bramucci, Boothwyn, PA (US); Robert A. Larossa, Chadds Ford, PA (US); Manjari Singh, West Chester, PA (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 648 days.

(21) Appl. No.: 12/643,019

(22) Filed: Dec. 21, 2009

(65) Prior Publication Data

US 2010/0167363 A1 Jul. 1, 2010

Related U.S. Application Data

(60) Provisional application No. 61/141,013, filed on Dec. 29, 2008.

(51) Int. Cl.

*C12P 7/16* (2006.01)
*C12N 1/15* (2006.01)
*C07H 21/00* (2006.01)
*C12N 15/00* (2006.01)
*C12P 21/00* (2006.01)

(52) U.S. Cl.

USPC ....... 435/254.2; 435/160; 435/440; 435/69.1; 435/320.1; 536/23.2

(58) Field of Classification Search

USPC .............................. 435/254.2, 160, 440, 69.1
See application file for complete search history.

(56) References Cited

U.S. PATENT DOCUMENTS

| | | | |
|---|---|---|---|
| 4,683,202 | A | 7/1987 | Mullis et al. |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0269823 | A1 | 10/2009 | Bramucci et al. |

OTHER PUBLICATIONS

Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
GenBank No. NC_004722.
GenBank No. NC_007347.
GenBank No. NP_010656.
GenBank No. NP_012550.
GenBank No. NP_013459.
GenBank No. NP_014051.
GenBank No. NP_015297.
GenBank No. NP_149189.
GenBank No. NP_149242.
GenBank No. NP_149325.
GenBank No. NP_347102.
GenBank No. NP_349314.
GenBank No. NP_349318.
GenBank No. NP_349476.1.
GenBank No. NP_349891.
GenBank No. NP_349892.
GenBank No. NP_390297.
GenBank No. NP_415911.
GenBank No. NP_416728.
GenBank No. NP_417484.
GenBank No. NP_418222.
GenBank No. NP_461346.
GenBank No. NP_830481.
GenBank No. P14697.
GenBank No. Q5EU90.
GenBank No. U29084.
GenBank No. U37135.
GenBank No. YP_026248.
GenBank No. YP_294481.
GenBank No. Z99113 obsolete and replaced by AL009126.
GenBank No. Z99115 obsolete and replaced by AL009126.
GenBank No. Z99118 obsolete and replaced by AL009126.
U.S. Appl. No. 12/569,636, filed Sep. 29, 2009, Flint et al. (CL4278).
Altschul, S. F., et al., J. Mol. Biol., 215:403 410 (1990).
Ashe et al. The EMBO Journal (2001) 20:6464-6474.
Bowman et al. (1997) Nature 387(6632 Suppl) 90-93.
Cutler et al. (2001) Mol. Biol. Cell 12:4103-4113.
da Silva et al. (2007) World J. of Microbiol. and Biotech. 23:697-704.
Deshpande, Mukund V., Appl. Biochem. Biotechnol., 36:227 (1992).
Dickinson (2008) Folia Microbiol. (Praha) 53:3-14.
Fagarasanu et al. (2006) Biochimica et Biophysica Acta (BBA)—Molecular Cell Research 1763:1669-1677.
Frohman et al., PNAS USA 85:8998 (1988).
Gagiano et al. (1999) Molecular Microbiology 31:103-116.
Gietz et al. (1995) Yeast 11:355-360.
Guo et al., J. Membr. Sci. 245, 199-210 (2004).
Higgins and Sharp, CABIOS. 5:151 153 (1989).
Jin et al. (2008) Molec. Biol. of the Cell 19:284-296.
Lo and Dranginis (1998) Mol. Bio. Cell 9:161-171.
Loh et al., Science 243:217 (1989).
Lorenz et al. Molec. Biol. of the Cell (2000) 11:183-199.
Martinez-Anaya et al. (2003) Journal of Cell Science 116, 3423-3431.
Mumberg et al. (1995) Gene 156:119-22.
Ohara et al., PNAS USA 86:5673 (1989).
Reid et al. (2002) Yeast 19(4):319-328.
Reed et al. (1989) J. Cell Sci. Suppl. 12:29-37.
Reynolds et al. (2001) Science 291:878-881.
Smirnova et al. Molecular and Cellular Bioloty (2005) 25:9340-9340.

(Continued)

*Primary Examiner* — Delia Ramirez
(74) *Attorney, Agent, or Firm* — Christine M. Lhulier

(57) ABSTRACT

Increasing tolerance to butanol in yeast has been accomplished by increasing activity of the filamentous growth response. Yeast with increased expression of MSS11p, a transcriptional activator of the filamentous growth response pathway had increased tolerance to isobutanol. These yeast may be used for improved butanol production.

6 Claims, 4 Drawing Sheets

(56) References Cited

OTHER PUBLICATIONS

Sulter et al., Arch. Microbiol. 153:485 489 (1990).
Tabor, S. et al., Proc. Acad. Sci. USA 82:1074 (1985).
Vancetto and Ceccato-Antonini (2007) J. Applied Micro. and Biotech. 75:111-115.
Van Ness and Chen, Nucl. Acids Res. 19:5143 5151 (1991).
Vinod et al. (2008) Mol Microbiol. 47(1):119-34.
Walker, et al., Proc. Natl. Acad. Sci. U.S.A., 89:392 (1992).
Aden et al. Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Ausubel, F. M. et al., In Current Protocols in Molecular Biology, published by Greene Publishing and Wiley-Interscience, 1987.
Amberg, Burke and Strathern, 2005, Methods in Yeast Genetics, Cold Spring Harbor Laboratory Press, Cold Spring Harbor, NY.
Bellion et al., Microb. Growth C1 Compd., [Int. Symp.], 7th (1993), 415 32. Editor(s): Murrell, J. Collin; Kelly, Don P. Publisher: Intercept, Andover, UK.
Biocomputing: Informatics and Genome Projects (Smith, D. W., Ed.) Academic: NY (1993).
Computational Molecular Biology (Lesk, A. M., Ed.) Oxford University: NY (1988).
Computer Analysis of Sequence Data, Part I (Griffin, A. M., and Griffin, H. G., Eds.) Humania: NJ (1994).
Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC (1994).
Methods in Enzymology, vol. 194, Guide to Yeast Genetics and Molecular and Cell Biology Part A, 2004, Christine Guthrie and Gerald R. Fink (Eds.), Elsevier Academic Press, San Diego, CA.
Methods in Yeast Genetics, 2005, Cold Spring Harbor Laboratory Press, Cold Spring Harbor, NY.
Rychlik, W., In Methods in Molecular Biology, White, B. A. Ed., (1993) vol. 15, pp. 31-39, PCR Protocols: Current Methods and Applications. Humania: Totowa, NJ.
Sambrook, J., Fritsch, E. F. and Maniatis, T. Molecular Cloning: A Laboratory Manual, 3rd ed., Cold Spring Harbor Laboratory: Cold Spring Harbor, NY (2001), particularly Chapter 11 and Table 11.1.
Sequence Analysis in Molecular Biology (von Heinje, G., Ed.) Academic (1987).
Sequence Analysis Primer (Gribskov, M. and Devereux, J., Eds.) Stockton: NY (1991).
Silhavy, T. J., Bennan, M. L. and Enquist, L. W. Experiments with Gene Fusions; Cold Spring Harbor Laboratory: Cold Spring Harbor, New York, 1984.
Thein and Wallace, "The use of oligonucleotides as specific hybridization probes in the Diagnosis of Genetic Disorders", in Human Genetic Diseases: A Practical Approach, K. E. Davis Ed., (1986) pp. 33 50, IRL: Herndon, VA.
Thomas D. Brock in Biotechnology: A Textbook of Industrial Microbiology, Second Edition (1989) Sinauer Associates, Inc., Sunderland, MA.
W. R. Pearson, Comput. Methods Genome Res., [Proc. Int. Symp.] (1994), Meeting Date 1992, 111-20. Editor(s): Suhai, Sandor. Plenum: New York, NY.
Yeast Protocols, Second Edition Wei Xiao, ed; Humana Press, Totowa, NJ (2006).

* cited by examiner

SEQUENCE LISTING

```
<160> NUMBER OF SEQ ID NOS: 73

<210> SEQ ID NO 1
<211> LENGTH: 1179
<212> TYPE: DNA
<213> ORGANISM: Clostridium acetobutylicum

<400> SEQUENCE: 1

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300

attataaaag caggagatgc tgacgtaata atagcaggtg gtatggaaaa tatgtctaga     360

gctccttact tagcgaataa cgctagatgg ggatatagaa tgggaaacgc taaatttgtt     420

gatgaaatga tcactgacgg attgtgggat gcatttaatg attaccacat gggaataaca     480

gcagaaaaca tagctgagag atggaacatt tcaagagaag aacaagatga gtttgctctt     540

gcatcacaaa aaaaagctga agaagctata aaatcaggtc aatttaaaga tgaaatagtt     600

cctgtagtaa ttaaaggcag aaagggagaa actgtagttg atacagatga gcaccctaga     660

tttggatcaa ctatagaagg acttgcaaaa ttaaaacctg ccttcaaaaa agatggaaca     720

gttacagctg gtaatgcatc aggattaaat gactgtgcag cagtacttgt aatcatgagt     780

gcagaaaaag ctaaagagct tggagtaaaa ccacttgcta agatagtttc ttatggttca     840

gcaggagttg acccagcaat aatgggatat ggacctttct atgcaacaaa agcagctatt     900

gaaaaagcag gttggacagt tgatgaatta gatttaatag aatcaaatga agcttttgca     960

gctcaaagtt tagcagtagc aaaagattta aaatttgata tgaataaagt aaatgtaaat    1020

ggaggagcta ttgcccttgg tcatccaatt ggagcatcag gtgcaagaat actcgttact    1080

cttgtacacg caatgcaaaa aagagatgca aaaaaaggct tagcaacttt atgtataggt    1140

ggcggacaag gaacagcaat attgctagaa aagtgctag                           1179

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30
```

```
Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390
```

```
<210> SEQ ID NO 3
<211> LENGTH: 1179
<212> TYPE: DNA
<213> ORGANISM: Clostridium acetobutylicum

<400> SEQUENCE: 3

atgagagatg tagtaatagt aagtgctgta agaactgcaa taggagcata tggaaaaaca      60
```

```
ttaaaggatg tacctgcaac agagttagga gctatagtaa taaaggaagc tgtaagaaga    120

gctaatataa atccaaatga gattaatgaa gttatttttg gaaatgtact tcaagctgga    180

ttaggccaaa acccagcaag acaagcagca gtaaaagcag gattaccttt agaaacacct    240

gcgtttacaa tcaataaggt ttgtggttca ggtttaagat ctataagttt agcagctcaa    300

attataaaag ctggagatgc tgataccatt gtagtaggtg gtatggaaaa tatgtctaga    360

tcaccatatt tgattaacaa tcagagatgg ggtcaaagaa tgggagatag tgaattagtt    420

gatgaaatga taaaggatgg tttgtgggat gcatttaatg gatatcatat gggagtaact    480

gcagaaaata ttgcagaaca atggaatata acaagagaag agcaagatga attttcactt    540

atgtcacaac aaaaagctga aaaagccatt aaaaatggag aatttaagga tgaaatagtt    600

cctgtattaa taaagactaa aaaaggtgaa atagtctttg atcaagatga atttcctaga    660

ttcggaaaca ctattgaagc attaagaaaa cttaaaccta ttttcaagga aaatggtact    720

gttacagcag gtaatgcatc cggattaaat gatggagctg cagcactagt aataatgagc    780

gctgataaag ctaacgctct cggaataaaa ccacttgcta agattacttc ttacggatca    840

tatggggtag atccatcaat aatgggatat ggagcttttt atgcaactaa agctgcctta    900

gataaaatta atttaaaacc tgaagactta gatttaattg aagctaacga ggcatatgct    960

tctcaaagta tagcagtaac tagagattta aatttagata tgagtaaagt taatgttaat   1020

ggtggagcta tagcacttgg acatccaata ggtgcatctg gtgcacgtat tttagtaaca   1080

ttactatacg ctatgcaaaa aagagattca aaaaaaggtc ttgctactct atgtattggt   1140

ggaggtcagg gaacagctct cgtagttgaa agagactaa                          1179
```

```
<210> SEQ ID NO 4
<211> LENGTH: 392
<212> TYPE: PRT
<213> ORGANISM: Clostridium acetobutylicum

<400> SEQUENCE: 4

Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
```

```
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390
```

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt      60

gcagctaaag gatttgaagt agtattaaga gatattaaag atgaatttgt tgatagagga     120

ttagatttta tcaataaaaa tctttctaaa ttagttaaaa aaggaaagat agaagaagct     180

actaaagttg aaatcttaac tagaatttcc ggaacagttg accttaatat ggcagctgat     240

tgcgatttag ttatagaagc agctgttgaa agaatggata ttaaaaagca gatttttgct     300

gacttagaca atatatgcaa gccagaaaca attcttgcat caaatacatc atcactttca     360

ataacagaag tggcatcagc aactaaaaga cctgataagg ttataggtat gcatttcttt     420

aatccagctc ctgttatgaa gcttgtagag gtaataagag gaatagctac atcacaagaa     480

acttttgatg cagttaaaga gacatctata gcaataggaa aagatcctgt agaagtagca     540

gaagcaccag gatttgttgt aaatagaata ttaataccaa tgattaatga agcagttggt     600

atattagcag aaggaatagc ttcagtagaa gacatagata aagctatgaa acttggagct     660

aatcacccaa tgggaccatt agaattaggt gattttatag gtcttgatat atgtcttgct     720

ataatggatg ttttatactc agaaactgga gattctaagt atagaccaca tacattactt     780

aagaagtatg taagagcagg atggcttgga agaaaatcag gaaaaggttt ctacgattat     840

tcaaaataa                                                             849
```

```
<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280


<210> SEQ ID NO 7
<211> LENGTH: 786
<212> TYPE: DNA
<213> ORGANISM: Clostridium acetobutylicum

<400> SEQUENCE: 7

atggaactaa acaatgtcat ccttgaaaag gaaggtaaag ttgctgtagt taccattaac      60

agacctaaag cattaaatgc gttaaatagt gatacactaa aagaaatgga ttatgttata     120

ggtgaaattg aaaatgatag cgaagtactt gcagtaattt taactggagc aggagaaaaa     180

tcatttgtag caggagcaga tatttctgag atgaaggaaa tgaataccat tgaaggtaga     240

aaattcggga tacttggaaa taaagtgttt agaagattag aacttcttga aaagcctgta     300

atagcagctg ttaatggttt tgctttagga ggcggatgcg aaatagctat gtcttgtgat     360
```

```
ataagaatag cttcaagcaa cgcaagattt ggtcaaccag aagtaggtct cggaataaca    420

cctggttttg gtggtacaca aagactttca agattagttg gaatgggcat ggcaaagcag    480

cttatattta ctgcacaaaa tataaaggca gatgaagcat taagaatcgg acttgtaaat    540

aaggtagtag aacctagtga attaatgaat acagcaaaag aaattgcaaa caaaattgtg    600

agcaatgctc cagtagctgt taagttaagc aaacaggcta ttaatagagg aatgcagtgt    660

gatattgata ctgctttagc atttgaatca gaagcatttg gagaatgctt ttcaacagag    720

gatcaaaagg atgcaatgac agctttcata gagaaaagaa aaattgaagg cttcaaaaat    780

agatag                                                               786
```

<210> SEQ ID NO 8
<211> LENGTH: 261
<212> TYPE: PRT
<213> ORGANISM: Clostridium acetobutylicum

<400> SEQUENCE: 8

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260
```

<210> SEQ ID NO 9
<211> LENGTH: 1197
<212> TYPE: DNA

<213> ORGANISM: Clostridium acetobutylicum

<400> SEQUENCE: 9

```
atgatagtaa aagcaaagtt tgtaaaagga tttatcagag atgtacatcc ttatggttgc     60
agaagggaag tactaaatca aatagattat tgtaagaagg ctattgggtt taggggacca    120
aagaaggttt taattgttgg agcctcatct gggtttggtc ttgctactag aatttcagtt    180
gcatttggag gtccagaagc tcacacaatt ggagtatcct atgaaacagg agctacagat    240
agaagaatag gaacagcggg atggtataat aacatatttt ttaaagaatt tgctaaaaaa    300
aaaggattag ttgcaaaaaa cttcattgag gatgcctttt ctaatgaaac caaagataaa    360
gttattaagt atataaagga tgaatttggt aaaatagatt tatttgttta tagtttagct    420
gcgcctagga gaaaggacta taaaactgga aatgtttata cttcaagaat aaaaacaatt    480
ttaggagatt ttgagggacc gactattgat gttgaaagag acgagattac tttaaaaaag    540
gttagtagtg ctagcattga agaaattgaa gaaactagaa aggtaatggg tggagaggat    600
tggcaagagt ggtgtgaaga gctgctttat gaagattgtt tttcggataa agcaactacc    660
atagcatact cgtatatagg atccccaaga acctacaaga tatatagaga aggtactata    720
ggaatagcta aaaaggatct tgaagataag gctaagctta taaatgaaaa acttaacaga    780
gttataggtg gtagagcctt tgtgtctgtg aataaagcat tagttacaaa agcaagtgca    840
tatattccaa cttttcctct ttatgcagct attttatata aggtcatgaa agaaaaaaat    900
attcatgaaa attgtattat gcaaattgag agaatgtttt ctgaaaaaat atattcaaat    960
gaaaaaatac aatttgatga caagggaaga ttaaggatgg acgatttaga gcttagaaaa   1020
gacgttcaag acgaagttga tagaatatgg agtaatatta ctcctgaaaa ttttaaggaa   1080
ttatctgatt ataagggata caaaaaagaa ttcatgaact taaacggttt tgatctagat   1140
ggggttgatt atagtaaaga cctggatata gaattattaa gaaaattaga accttaa      1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
```

```
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
        355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395
```

<210> SEQ ID NO 11
<211> LENGTH: 1407
<212> TYPE: DNA
<213> ORGANISM: Clostridium beijerinckii

<400> SEQUENCE: 11

```
atgaataaag acacactaat acctacaact aaagatttaa aagtaaaaac aaatggtgaa     60

aacattaatt taaagaacta caaggataat tcttcatgtt tcggagtatt cgaaaatgtt    120

gaaaatgcta taagcagcgc tgtacacgca caaaagatat tatcccttca ttatacaaaa    180

gagcaaagag aaaaaatcat aactgagata agaaaggccg cattacaaaa taaagaggtc    240

ttggctacaa tgattctaga agaaacacat atgggaagat atgaggataa aatattaaaa    300

catgaattgg tagctaaata tactcctggt acagaagatt taactactac tgcttggtca    360

ggtgataatg gtcttacagt tgtagaaatg tctccatatg gtgttatagg tgcaataact    420

ccttctacga atccaactga aactgtaata tgtaatagca taggcatgat agctgctgga    480

aatgctgtag tatttaacgg acacccatgc gctaaaaaat gtgttgcctt tgctgttgaa    540

atgataaata aggcaattat ttcatgtggc ggtcctgaaa atctagtaac aactataaaa    600

aatccaacta tggagtctct agatgcaatt attaagcatc cttcaataaa acttctttgc    660

ggaactgggg gtccaggaat ggtaaaaacc ctcttaaatt ctggtaagaa agctataggt    720

gctggtgctg gaaatccacc agttattgta gatgatactg ctgatataga aaaggctggt    780
```

```
aggagcatca ttgaaggctg ttcttttgat aataatttac cttgtattgc agaaaaagaa    840

gtatttgttt ttgagaatgt tgcagatgat ttaatatcta acatgctaaa aaataatgct    900

gtaattataa atgaagatca agtatcaaaa ttaatagatt tagtattaca aaaaaataat    960

gaaactcaag aatactttat aaacaaaaaa tgggtaggaa aagatgcaaa attattctta   1020

gatgaaatag atgttgagtc tccttcaaat gttaaatgca taatctgcga agtaaatgca   1080

aatcatccat ttgttatgac agaactcatg atgccaatat tgccaattgt aagagttaaa   1140

gatatagatg aagctattaa atatgcaaag atagcagaac aaaatagaaa acatagtgcc   1200

tatatttatt ctaaaaatat agacaaccta aatagatttg aaagagaaat agatactact   1260

atttttgtaa agaatgctaa atcttttgct ggtgttggtt atgaagcaga aggatttaca   1320

actttcacta ttgctggatc tactggtgag ggaataacct ctgcaaggaa ttttacaaga   1380

caaagaagat gtgtacttgc cggctaa                                       1407
```

```
<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
```

```
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465


<210> SEQ ID NO 13
<211> LENGTH: 1215
<212> TYPE: DNA
<213> ORGANISM: Clostridium acetobutylicum

<400> SEQUENCE: 13

atggttgatt tcgaatattc aataccaact agaatttttt tcggtaaaga taagataaat      60

gtacttggaa gagagcttaa aaaatatggt tctaaagtgc ttatagttta tggtggagga     120

agtataaaga gaaatggaat atatgataaa gctgtaagta tacttgaaaa aaacagtatt     180

aaattttatg aacttgcagg agtagagcca aatccaagag taactacagt tgaaaaagga     240

gttaaaatat gtagagaaaa tggagttgaa gtagtactag ctataggtgg aggaagtgca     300

atagattgcg caaaggttat agcagcagca tgtgaatatg atggaaatcc atgggatatt     360

gtgttagatg gctcaaaaat aaaaagggtg cttcctatag ctagtatatt aaccattgct     420

gcaacaggat cagaaatgga tacgtgggca gtaataaata atatggatac aaacgaaaaa     480

ctaattgcgg cacatccaga tatggctcct aagttttcta tattagatcc aacgtatacg     540

tataccgtac ctaccaatca aacagcagca ggaacagctg atattatgag tcatatattt     600

gaggtgtatt ttagtaatac aaaaacagca tatttgcagg atagaatggc agaagcgtta     660

ttaagaactt gtattaaata tggaggaata gctcttgaga agccggatga ttatgaggca     720

agagccaatc taatgtgggc ttcaagtctt gcgataaatg gacttttaac atatggtaaa     780

gacactaatt ggagtgtaca cttaatggaa catgaattaa gtgcttatta cgacataaca     840

cacggcgtag ggcttgcaat tttaacacct aattggatgg agtatatttt aaataatgat     900

acagtgtaca agtttgttga atatggtgta aatgtttggg gaatagacaa agaaaaaaat     960
```

```
cactatgaca tagcacatca agcaatacaa aaaacaagag attactttgt aaatgtacta   1020

ggtttaccat ctagactgag agatgttgga attgaagaag aaaaattgga cataatggca   1080

aaggaatcag taaagcttac aggaggaacc ataggaaacc taagaccagt aaacgcctcc   1140

gaagtcctac aaatattcaa aaaatctgtg taaaacgcct ccgaagtcct acaaatattc   1200

aaaaaatctg tgtaa                                                    1215


<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
```

```
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390


<210> SEQ ID NO 15
<211> LENGTH: 1170
<212> TYPE: DNA
<213> ORGANISM: Clostridium acetobutylicum

<400> SEQUENCE: 15

atgctaagtt ttgattattc aataccaact aaagtttttt ttggaaaagg aaaaatagac      60

gtaattggag aagaaattaa gaaatatggc tcaagagtgc ttatagttta tggcggagga     120

agtataaaaa ggaacggtat atatgataga gcaacagcta tattaaaaga aaacaatata     180

gctttctatg aactttcagg agtagagcca aatcctagga taacaacagt aaaaaaaggc     240

atagaaatat gtagagaaaa taatgtggat ttagtattag caatagggggg aggaagtgca     300

atagactgtt ctaaggtaat tgcagctgga gtttattatg atggcgatac atgggacatg     360

gttaaagatc catctaaaat aactaaagtt cttccaattg caagtatact tactctttca     420

gcaacagggt ctgaaatgga tcaaattgca gtaatttcaa atatggagac taatgaaaag     480

cttggagtag gacatgatga tatgagacct aaattttcag tgttagatcc tacatatact     540

tttacagtac ctaaaaatca aacagcagcg ggaacagctg acattatgag tcacaccttt     600

gaatcttact ttagtggtgt tgaaggtgct tatgtgcagg acggtatagc agaagcaatc     660

ttaagaacat gtataaagta tggaaaaata gcaatggaga agactgatga ttacgaggct     720

agagctaatt tgatgtgggc ttcaagttta gctataaatg gtctattatc acttggtaag     780

gatagaaaat ggagttgtca tcctatggaa cacgagttaa gtgcatatta tgatataaca     840

catggtgtag gacttgcaat tttaacacct aattggatgg aatatattct aaatgacgat     900

acacttcata aatttgtttc ttatggaata aatgtttggg gaatagacaa gaacaaagat     960

aactatgaaa tagcacgaga ggctattaaa aatacgagag aatactttaa ttcattgggt    1020

attccttcaa agcttagaga agttggaata ggaaaagata aactagaact aatggcaaag    1080

caagctgtta gaaattctgg aggaacaata ggaagtttaa gaccaataaa tgcagaggat    1140

gttcttgaga tatttaaaaa atcttattaa                                     1170


<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
```

```
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385


<210> SEQ ID NO 17
<211> LENGTH: 780
<212> TYPE: DNA
<213> ORGANISM: Klebsiella pneumoniae

<400> SEQUENCE: 17

atgaatcatt ctgctgaatg cacctgcgaa gagagtctat gcgaaaccct gcgggcgttt      60

tccgcgcagc atcccgagag cgtgctctat cagacatcgc tcatgagcgc cctgctgagc     120

ggggtttacg aaggcagcac caccatcgcg gacctgctga aacacggcga tttcggcctc     180

ggcaccttta atgagctgga cggggagctg atcgccttca gcagtcaggt ctatcagctg     240
```

```
cgcgccgacg gcagcgcgcg caaagcccag ccggagcaga aaacgccgtt cgcggtgatg    300

acctggttcc agccgcagta ccggaaaacc tttgaccatc cggtgagccg ccagcagctg    360

cacgaggtga tcgaccagca aatcccctct gacaacctgt tctgcgccct gcgcatcgac    420

ggccatttcc gccatgccca tacccgcacc gtgccgcgcc agacgccgcc gtaccgggcg    480

atgaccgacg tcctcgacga tcagccggtg ttccgcttta accagcgcga aggggtgctg    540

gtcggcttcc ggaccccgca gcatatgcag gggatcaacg tcgccgggta tcacgagcac    600

tttattaccg atgaccgcaa aggcggcggt cacctgctgg attaccagct cgaccatggg    660

gtgctgacct tcggcgaaat tcacaagctg atgatcgacc tgcccgccga cagcgcgttc    720

ctgcaggcta atctgcatcc cgataatctc gatgccgcca tccgttccgt agaaagttaa    780
```

```
<210> SEQ ID NO 18
<211> LENGTH: 259
<212> TYPE: PRT
<213> ORGANISM: Klebsiella pneumoniae

<400> SEQUENCE: 18

Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser

<210> SEQ ID NO 19
<211> LENGTH: 1680
```

<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag     60
ctggaagctc agggagtacg ccaggtgttc ggcatccccg gcgccaaaat tgacaaggtc    120
ttcgactcac tgctggattc ctcgattcgc attattccgg tacgccacga agccaacgcc    180
gcgtttatgg ccgccgccgt cggacgcatt accggcaaag cgggcgtggc gctggtcacc    240
tccggtccgg gctgttccaa cctgatcacc ggcatggcca ccgcgaacag cgaaggcgac    300
ccggtggtgg ccctgggcgg cgcggtaaaa cgcgccgata aagcgaagca ggtccaccag    360
agtatggata cggtggcgat gttcagcccg gtcaccaaat acgccgtcga ggtgacggcg    420
ccggatgcgc tggcggaagt ggtctccaac gccttccgcg ccgccgagca gggccggccg    480
ggcagcgcgt tcgttagcct gccgcaggat gtggtcgatg gcccggtcag cggcaaagtg    540
ctgccggcca gcggggcccc gcagatgggc gccgcgccgg atgatgccat cgaccaggtg    600
gcgaagctta tcgcccaggc gaagaacccg atcttcctgc tcggcctgat ggccagccag    660
ccggaaaaca gcaaggcgct gcgccgtttg ctggagacca gccatattcc agtcaccagc    720
acctatcagg ccgccggagc ggtgaatcag gataacttct ctcgcttcgc cggccgggtt    780
gggctgttta acaaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtggaca tgggcagctt ccatatctgg   1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga aagccaacgt actgcacctg atctgggtcg ataacggcta caacatggtg   1440
gccattcagg aagagaaaaa ataccagcgc ctgtccggcg tcgagttcgg gccgatggat   1500
tttaaagcct atgccgaatc cttcggcgcg aaagggtttg ccgtggaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680
```

<210> SEQ ID NO 20
<211> LENGTH: 559
<212> TYPE: PRT
<213> ORGANISM: Klebsiella pneumoniae

<400> SEQUENCE: 20

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60
```

```
Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
```

```
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555


<210> SEQ ID NO 21
<211> LENGTH: 771
<212> TYPE: DNA
<213> ORGANISM: Klebsiella pneumoniae

<400> SEQUENCE: 21

atgaaaaaag tcgcacttgt taccggcgcc ggccagggga ttggtaaagc tatcgccctt      60

cgtctggtga aggatggatt tgccgtggcc attgccgatt ataacgacgc caccgccaaa     120

gcggtcgcct cggaaatcaa ccaggccggc ggacacgccg tggcggtgaa agtggatgtc     180

tccgaccgcg atcaggtatt tgccgccgtt gaacaggcgc gcaaaacgct gggcggcttc     240

gacgtcatcg tcaataacgc cggtgtggca ccgtctacgc cgatcgagtc cattaccccg     300

gagattgtcg acaaagtcta caacatcaac gtcaaagggg tgatctgggg tattcaggcg     360

gcggtcgagg cctttaagaa agaggggcac ggcgggaaaa tcatcaacgc ctgttcccag     420

gccggccacg tcggcaaccc ggagctggcg gtgtatagct ccagtaaatt cgcggtacgc     480

ggcttaaccc agaccgccgc tcgcgacctc gcgccgctgg gcatcacggt caacggctac     540

tgcccgggga ttgtcaaaac gccaatgtgg gccgaaattg accgccaggt gtccgaagcc     600

gccggtaaac cgctgggcta cggtaccgcc gagttcgcca aacgcatcac tctcggtcgt     660

ctgtccgagc cggaagatgt cgccgcctgc gtctcctatc ttgccagccc ggattctgat     720

tacatgaccg gtcagtcgtt gctgatcgac ggcgggatgg tatttaacta a              771


<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125
```

```
Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255


<210> SEQ ID NO 23
<211> LENGTH: 1665
<212> TYPE: DNA
<213> ORGANISM: Klebsiella oxytoca

<400> SEQUENCE: 23

atgagatcga aaagatttga agcactggcg aaacgccctg tgaatcagga cggcttcgtt      60

aaggagtgga tcgaagaagg ctttatcgcg atggaaagcc cgaacgaccc aaaaccgtcg     120

attaaaatcg ttaacggcgc ggtgaccgag ctggacggga aaccggtaag cgattttgac     180

ctgatcgacc actttatcgc ccgctacggt atcaacctga accgcgccga agaagtgatg     240

gcgatggatt cggtcaagct ggccaacatg ctgtgcgatc cgaacgttaa acgcagcgaa     300

atcgtcccgc tgaccaccgc gatgacgccg gcgaaaattg tcgaagtggt ttcgcatatg     360

aacgtcgtcg agatgatgat ggcgatgcag aaaatgcgcg cccgccgcac cccgtcccag     420

caggcgcacg tcaccaacgt caaagataac ccggtacaga ttgccgccga cgccgccgaa     480

ggggcatggc gcggatttga cgaacaggaa accaccgttg cggtagcgcg ctatgcgccg     540

ttcaacgcca tcgcgctgct ggtgggctcg caggtaggcc gtccgggcgt gctgacgcag     600

tgctcgctgg aagaagccac cgagctgaag ctcggcatgc tgggccacac ctgctacgcc     660

gaaaccatct ccgtctacgg caccgagccg gtctttaccg acggcgacga cacgccgtgg     720

tcgaagggct tcctcgcctc gtcctacgcc tctcgcgggc tgaaaatgcg ctttacctcc     780

ggctccggct cggaagtgca gatgggctac gccgaaggca aatccatgct ttatctggaa     840

gcgcgctgca tctacatcac caaagccgcg ggcgtacagg gtctgcaaaa cggttccgta     900

agctgcatcg gcgtgccgtc tgcggtgcct tccggcattc gcgcggtgct ggcggaaaac     960

ctgatctgtt cgtcgctgga tctggagtgc gcctccagca acgaccagac cttcacccac    1020

tccgatatgc gtcgtaccgc gcgcctgctg atgcagttcc tgccgggcac cgactttatc    1080

tcctccggtt attccgcggt gccgaactac gacaacatgt tcgccggctc caacgaagat    1140

gccgaagact ttgacgacta caacgtcatc cagcgcgacc tgaaggtgga cggcggtttg    1200

cgtccggttc gcgaagagga cgtcatcgcc atccgtaaca aagccgcccg cgcgctgcag    1260

gccgtgtttg ccggaatggg gctgccgccg attaccgatg aagaagttga agccgcgacc    1320

tacgcccacg gttcgaaaga tatgccggag cgcaacatcg tcgaagacat caagttcgcc    1380

caggaaatca tcaataaaaa ccgcaacggt ctggaagtgg tgaaagcgct ggcgcagggc    1440
```

```
ggattcaccg acgtggccca ggacatgctc aacatccaga aagctaagct gaccggggac   1500

tacctgcata cctccgcgat tatcgtcggc gacgggcagg tgctgtcagc cgtcaacgac   1560

gtcaacgact atgccggtcc ggcaacgggc tatcgcctgc agggcgaacg ctgggaagag   1620

attaaaaaca tccctggcgc tcttgatccc aacgagattg attaa                   1665


<210> SEQ ID NO 24
<211> LENGTH: 554
<212> TYPE: PRT
<213> ORGANISM: Klebsiella oxytoca

<400> SEQUENCE: 24

Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
```

```
        340                 345                 350

Phe Leu Pro Gly Thr Asp Phe Ile Ser Ser Gly Tyr Ser Ala Val Pro
    355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Ile Asp
545                 550
```

<210> SEQ ID NO 25
<211> LENGTH: 675
<212> TYPE: DNA
<213> ORGANISM: Klebsiella oxytoca

<400> SEQUENCE: 25

```
atggaaatta atgaaaaatt gctgcgccag ataattgaag acgtgctcag cgagatgaag     60

ggcagcgata aaccggtctc gtttaatgcg ccggcggcct ccgcggcgcc ccaggccacg    120

ccgcccgccg gcgacggctt cctgacggaa gtgggcgaag cgcgtcaggg aacccagcag    180

gacgaagtga ttatcgccgt cggcccggct ttcggcctgg cgcagaccgt caatatcgtc    240

ggcatcccgc ataagagcat tttgcgcgaa gtcattgccg gtattgaaga agaaggcatt    300

aaggcgcgcg tgattcgctg ctttaaatcc tccgacgtgg ccttcgtcgc cgttgaaggt    360

aatcgcctga gcggctccgg catctctatc ggcatccagt cgaaaggcac cacggtgatc    420

caccagcagg ggctgccgcc gctctctaac ctggagctgt tcccgcaggc gccgctgctg    480

accctggaaa cctatcgcca gatcggcaaa aacgccgccc gctatgcgaa acgcgaatcg    540

ccgcagccgg tcccgacgct gaatgaccag atggcgcggc cgaagtacca ggcgaaatcg    600

gccattttgc acattaaaga gaccaagtac gtggtgacgg gcaaaaaccc gcaggaactg    660

cgcgtggcgc tttga                                                     675
```

<210> SEQ ID NO 26
<211> LENGTH: 224
<212> TYPE: PRT
<213> ORGANISM: Klebsiella oxytoca

<400> SEQUENCE: 26

```
Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60

Ile Ala Val Gly Pro Ala Phe Gly Leu Ala Gln Thr Val Asn Ile Val
65                  70                  75                  80

Gly Ile Pro His Lys Ser Ile Leu Arg Glu Val Ile Ala Gly Ile Glu
                85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
        115                 120                 125

Ser Ile Gly Ile Gln Ser Lys Gly Thr Thr Val Ile His Gln Gln Gly
    130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
        195                 200                 205

Lys Tyr Val Val Thr Gly Lys Asn Pro Gln Glu Leu Arg Val Ala Leu
    210                 215                 220
```

<210> SEQ ID NO 27
<211> LENGTH: 522
<212> TYPE: DNA
<213> ORGANISM: Klebsiella oxytoca

<400> SEQUENCE: 27

```
atgaataccg acgcaattga atcgatggta cgcgacgtat tgagccgcat gaacagcctg      60

cagggcgagg cgcctgcggc ggctccggcg gctggcggcg cgtcccgtag cgccagggtc     120

agcgactacc cgctggcgaa caagcacccg gaatgggtga aaaccgccac caataaaacg     180

ctggacgact ttacgctgga aaacgtgctg agcaataaag tcaccgccca ggatatgcgt     240

attaccccgg aaaccctgcg cttacaggct tctattgcca aagacgcggg ccgcgaccgg     300

ctggcgatga acttcgagcg cgccgccgag ctgaccgcgg taccggacga tcgcattctt     360

gaaatctaca acgccctccg cccctatcgc tcgacgaaag aggagctgct ggcgatcgcc     420

gacgatctcg aaagccgcta tcaggcgaag atttgcgccg ctttcgttcg cgaagcggcc     480

acgctgtacg tcgagcgtaa aaaactcaaa ggcgacgatt aa                        522
```

<210> SEQ ID NO 28
<211> LENGTH: 173
<212> TYPE: PRT
<213> ORGANISM: Klebsiella oxytoca

<400> SEQUENCE: 28

```
Met Asn Thr Asp Ala Ile Glu Ser Met Val Arg Asp Val Leu Ser Arg
1               5                   10                  15
```

```
Met Asn Ser Leu Gln Gly Glu Ala Pro Ala Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170
```

<210> SEQ ID NO 29
<211> LENGTH: 1041
<212> TYPE: DNA
<213> ORGANISM: Rhodococcus ruber

<400> SEQUENCE: 29

```
atgaaagccc tccagtacac cgagatcggc tccgagccgg tcgtcgtcga cgtccccacc     60

ccggcgcccg ggccgggtga gatcctgctg aaggtcaccg cggccggctt gtgccactcg    120

gacatcttcg tgatggacat gccggcagag cagtacatct acggtcttcc cctcaccctc    180

ggccacgagg gcgtcggcac cgtcgccgaa ctcggcgccg gcgtcaccgg attcgagacg    240

ggggacgccg tcgccgtgta cgggccgtgg gggtgcggtg cgtgccacgc gtgcgcgcgc    300

ggccgggaga actactgcac ccgcgccgcc gagctgggca tcaccccgcc cggtctcggc    360

tcgcccgggt cgatggccga gtacatgatc gtcgactcgg cgcgccacct cgtcccgatc    420

ggggacctcg accccgtcgc ggcggttccg ctcaccgacg cgggcctgac gccgtaccac    480

gcgatctcgc gggtcctgcc cctgctggga cccggctcga ccgcggtcgt catcggggtc    540

ggcggactcg ggcacgtcgg catccagatc ctgcgcgccg tcagcgcggc ccgcgtgatc    600

gccgtcgatc tcgacgacga ccgactcgcg ctcgcccgcg aggtcggcgc cgacgcggcg    660

gtgaagtcgg gcgccggggc ggcggacgcg atccgggagc tgaccggcgg tgagggcgcg    720

acggcggtgt tcgacttcgt cggcgcccag tcgacgatcg acacggcgca gcaggtggtc    780

gcgatcgacg ggcacatctc ggtggtcggc atccatgccg gcgcccacgc caaggtcggc    840

ttcttcatga tcccgttcgg cgcgtccgtc gtgacgccgt actggggcac gcggtccgag    900

ctgatggacg tcgtggacct ggcccgtgcc ggccggctcg acatccacac cgagacgttc    960

accctcgacg agggacccac ggcctaccgg cggctacgcg agggcagcat ccgcggccgc   1020

ggggtggtcg tcccgggctg a                                             1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345
```

<210> SEQ ID NO 31
<211> LENGTH: 1476
<212> TYPE: DNA
<213> ORGANISM: Escherichia coli

<400> SEQUENCE: 31

```
atggctaact acttcaatac actgaatctg cgccagcagc tggcacagct gggcaaatgt      60

cgctttatgg gccgcgatga attcgccgat ggcgcgagct accttcaggg taaaaaagta     120
```

-continued

```
gtcatcgtcg gctgtggcgc acagggtctg aaccagggcc tgaacatgcg tgattctggt    180

ctcgatatct cctacgctct gcgtaaagaa gcgattgccg agaagcgcgc gtcctggcgt    240

aaagcgaccg aaaatggttt taaagtgggt acttacgaag aactgatccc acaggcggat    300

ctggtgatta acctgacgcc ggacaagcag cactctgatg tagtgcgcac cgtacagcca    360

ctgatgaaag acggcgcggc gctgggctac tcgcacggtt tcaacatcgt cgaagtgggc    420

gagcagatcc gtaaagatat caccgtagtg atggttgcgc cgaaatgccc aggcaccgaa    480

gtgcgtgaag agtacaaacg tgggttcggc gtaccgacgc tgattgccgt tcacccggaa    540

aacgatccga aaggcgaagg catggcgatt gccaaagcct gggcggctgc aaccggtggt    600

caccgtgcgg gtgtgctgga atcgtccttc gttgcggaag tgaaatctga cctgatgggc    660

gagcaaacca tcctgtgcgg tatgttgcag gctggctctc tgctgtgctt cgacaagctg    720

gtggaagaag gtaccgatcc agcatacgca gaaaaactga ttcagttcgg ttgggaaacc    780

atcaccgaag cactgaaaca gggcggcatc accctgatga tggaccgtct ctctaacccg    840

gcgaaactgc gtgcttatgc gctttctgaa cagctgaaag agatcatggc acccctgttc    900

cagaaacata tggacgacat catctccggc gaattctctt ccggtatgat ggcggactgg    960

gccaacgatg ataagaaact gctgacctgg cgtgaagaga ccggcaaaac cgcgtttgaa   1020

accgcgccgc agtatgaagg caaaatcggc gagcaggagt acttcgataa aggcgtactg   1080

atgattgcga tggtgaaagc gggcgttgaa ctggcgttcg aaaccatggt cgattccggc   1140

atcattgaag agtctgcata ttatgaatca ctgcacgagc tgccgctgat tgccaacacc   1200

atcgcccgta agcgtctgta cgaaatgaac gtggttatct ctgataccgc tgagtacggt   1260

aactatctgt tctcttacgc ttgtgtgccg ttgctgaaac cgtttatggc agagctgcaa   1320

ccgggcgacc tgggtaaagc tattccggaa ggcgcggtag ataacgggca actgcgtgat   1380

gtgaacgaag cgattcgcag ccatgcgatt gagcaggtag gtaagaaact gcgcggctat   1440

atgacagata tgaaacgtat tgctgttgcg ggttaa                              1476
```

<210> SEQ ID NO 32
<211> LENGTH: 491
<212> TYPE: PRT
<213> ORGANISM: Escherichia coli

<400> SEQUENCE: 32

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140
```

```
Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 33
<211> LENGTH: 1851
<212> TYPE: DNA
<213> ORGANISM: Escherichia coli

<400> SEQUENCE: 33

```
atgcctaagt accgttccgc caccaccact catggtcgta atatggcggg tgctcgtgcg      60

ctgtggcgcg ccaccggaat gaccgacgcc gatttcggta agccgattat cgcggttgtg     120

aactcgttca cccaatttgt accgggtcac gtccatctgc gcgatctcgg taaactggtc     180
```

```
gccgaacaaa ttgaagcggc tggcggcgtt gccaaagagt tcaacaccat tgcggtggat    240

gatgggattg ccatgggcca cgggggggatg ctttattcac tgccatctcg cgaactgatc    300

gctgattccg ttgagtatat ggtcaacgcc cactgcgccg acgccatggt ctgcatctct    360

aactgcgaca aaatcacccc ggggatgctg atggcttccc tgcgcctgaa tattccggtg    420

atctttgttt ccggcggccc gatggaggcc gggaaaacca aactttccga tcagatcatc    480

aagctcgatc tggttgatgc gatgatccag ggcgcagacc cgaaagtatc tgactcccag    540

agcgatcagg ttgaacgttc cgcgtgtccg acctgcggtt cctgctccgg gatgtttacc    600

gctaactcaa tgaactgcct gaccgaagcg ctgggcctgt cgcagccggg caacggctcg    660

ctgctggcaa cccacgccga ccgtaagcag ctgttcctta atgctggtaa acgcattgtt    720

gaattgacca aacgttatta cgagcaaaac gacgaaagtg cactgccgcg taatatcgcc    780

agtaaggcgg cgtttgaaaa cgccatgacg ctggatatcg cgatgggtgg atcgactaac    840

accgtacttc acctgctggc ggcggcgcag gaagcggaaa tcgacttcac catgagtgat    900

atcgataagc tttcccgcaa ggttccacag ctgtgtaaag ttgcgccgag cacccagaaa    960

taccatatgg aagatgttca ccgtgctggt ggtgttatcg gtattctcgg cgaactggat   1020

cgcgcggggt tactgaaccg tgatgtgaaa aacgtacttg gcctgacgtt gccgcaaacg   1080

ctggaacaat acgacgttat gctgacccag gatgacgcgg taaaaaatat gttccgcgca   1140

ggtcctgcag gcattcgtac cacacaggca ttctcgcaag attgccgttg ggatacgctg   1200

gacgacgatc gcgccaatgg ctgtatccgc tcgctggaac acgcctacag caaagacggc   1260

ggcctggcgg tgctctacgg taactttgcg gaaaacggct gcatcgtgaa aacggcaggc   1320

gtcgatgaca gcatcctcaa attcaccggc ccggcgaaag tgtacgaaag ccaggacgat   1380

gcggtagaag cgattctcgg cggtaaagtt gtcgccggag atgtggtagt aattcgctat   1440

gaaggcccga aaggcggtcc ggggatgcag gaaatgctct acccaaccag cttcctgaaa   1500

tcaatgggtc tcggcaaagc ctgtgcgctg atcaccgacg gtcgtttctc tggtggcacc   1560

tctggtcttt ccatcggcca cgtctcaccg gaagcggcaa gcggcggcag cattggcctg   1620

attgaagatg gtgacctgat cgctatcgac atcccgaacc gtggcattca gttacaggta   1680

agcgatgccg aactggcggc gcgtcgtgaa gcgcaggacg ctcgaggtga caaagcctgg   1740

acgccgaaaa atcgtgaacg tcaggtctcc tttgccctgc gtgcttatgc cagcctggca   1800

accagcgccg acaaaggcgc ggtgcgcgat aaatcgaaac tgggggggtta a           1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80
```

```
Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510
```

```
Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615
```

<210> SEQ ID NO 35
<211> LENGTH: 1647
<212> TYPE: DNA
<213> ORGANISM: Lactococcus lactis

<400> SEQUENCE: 35

```
atgtatactg tgggggatta cctgctggat cgcctgcacg aactggggat tgaagaaatt     60

ttcggtgtgc caggcgatta taacctgcag ttcctggacc agattatctc gcacaaagat    120

atgaagtggg tcggtaacgc caacgaactg aacgcgagct atatggcaga tggttatgcc    180

cgtaccaaaa aagctgctgc gtttctgacg acctttggcg ttggcgaact gagcgccgtc    240

aacggactgg caggaagcta cgccgagaac ctgccagttg tcgaaattgt tgggtcgcct    300

acttctaagg ttcagaatga aggcaaattt gtgcaccata ctctggctga tggggatttt    360

aaacatttta tgaaaatgca tgaaccggtt actgcggccc gcacgctgct gacagcagag    420

aatgctacgg ttgagatcga ccgcgtcctg tctgcgctgc tgaaagagcg caagccggta    480

tatatcaatc tgcctgtcga tgttgccgca gcgaaagccg aaaagccgtc gctgccactg    540

aaaaaagaaa acagcacctc caatacatcg gaccaggaaa ttctgaataa aatccaggaa    600

tcactgaaga atgcgaagaa accgatcgtc atcaccggac atgagatcat ctcttttggc    660

ctggaaaaaa cggtcacgca gttcatttct aagaccaaac tgcctatcac caccctgaac    720

ttcggcaaat ctagcgtcga tgaagcgctg ccgagttttc tgggtatcta taatggtacc    780

ctgtccgaac cgaacctgaa agaattcgtc gaaagcgcgg actttatcct gatgctgggc    840

gtgaaactga cggatagctc cacaggcgca tttacccacc atctgaacga gaataaaatg    900

atttccctga atatcgacga aggcaaaatc tttaacgagc gcatccagaa cttcgatttt    960

gaatctctga ttagttcgct gctggatctg tccgaaattg agtataaagg taaatatatt   1020

gataaaaaac aggaggattt tgtgccgtct aatgcgctgc tgagtcagga tcgtctgtgg   1080

caagccgtag aaaacctgac acagtctaat gaaacgattg ttgcggaaca gggaacttca   1140

tttttcggcg cctcatccat ttttctgaaa tccaaaagcc atttcattgg ccaaccgctg   1200

tgggggagta ttggttatac ctttccggcg gcgctgggtt cacagattgc agataaggaa   1260

tcacgccatc tgctgtttat tggtgacggc agcctgcagc tgactgtcca ggaactgggg   1320

ctggcgatcc gtgaaaaaat caatccgatt tgctttatca tcaataacga cggctacacc   1380

gtcgaacgcg aaattcatgg accgaatcaa agttacaatg acatcccgat gtggaactat   1440

agcaaactgc cggaatcctt tggcgcgaca gaggatcgcg tggtgagtaa aattgtgcgt   1500
```

```
acggaaaacg aatttgtgtc ggttatgaaa gaagcgcagg ctgacccgaa tcgcatgtat   1560

tggattgaac tgatcctggc aaaagaaggc gcaccgaaag ttctgaaaaa gatggggaaa   1620

ctgtttgcgg agcaaaataa aagctaa                                       1647


<210> SEQ ID NO 36
<211> LENGTH: 548
<212> TYPE: PRT
<213> ORGANISM: Lactococcus lactis

<400> SEQUENCE: 36

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350
```

```
Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 37
<211> LENGTH: 1164
<212> TYPE: DNA
<213> ORGANISM: Escherichia coli

<400> SEQUENCE: 37

```
atgaacaact ttaatctgca caccccaacc cgcattctgt ttggtaaagg cgcaatcgct      60

ggtttacgcg aacaaattcc tcacgatgct cgcgtattga ttacctacgg cggcggcagc     120

gtgaaaaaaa ccggcgttct cgatcaagtt ctggatgccc tgaaaggcat ggacgtgctg     180

gaatttggcg gtattgagcc aaacccggct tatgaaacgc tgatgaacgc cgtgaaactg     240

gttcgcgaac agaaagtgac tttcctgctg gcggttggcg gcggttctgt actggacggc     300

accaaattta tcgccgcagc ggctaactat ccggaaaata tcgatccgtg gcacattctg     360

caaacgggcg gtaaagagat taaaagcgcc atcccgatgg gctgtgtgct gacgctgcca     420

gcaaccggtt cagaatccaa cgcaggcgcg gtgatctccc gtaaaaccac aggcgacaag     480

caggcgttcc attctgccca tgttcagccg gtatttgccg tgctcgatcc ggtttatacc     540

tacaccctgc cgccgcgtca ggtggctaac ggcgtagtgg acgcctttgt acacaccgtg     600

gaacagtatg ttaccaaacc ggttgatgcc aaaattcagg accgtttcgc agaaggcatt     660

ttgctgacgc taatcgaaga tggtccgaaa gccctgaaag agccagaaaa ctacgatgtg     720

cgcgccaacg tcatgtgggc ggcgactcag gcgctgaacg gtttgattgg cgctggcgta     780

ccgcaggact gggcaacgca tatgctgggc cacgaactga ctgcgatgca cggtctggat     840

cacgcgcaaa cactggctat cgtcctgcct gcactgtgga atgaaaaacg cgataccaag     900

cgcgctaagc tgctgcaata tgctgaacgc gtctggaaca tcactgaagg ttccgatgat     960

gagcgtattg acgccgcgat tgccgcaacc cgcaatttct ttgagcaatt aggcgtgccg    1020
```

```
acccacctct ccgactacgg tctggacggc agctccatcc cggctttgct gaaaaaactg   1080

gaagagcacg gcatgaccca actgggcgaa aatcatgaca ttacgttgga tgtcagccgc   1140

cgtatatacg aagccgcccg ctaa                                           1164


<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350
```

```
Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 39
<211> LENGTH: 1197
<212> TYPE: DNA
<213> ORGANISM: Saccharomyces cerevisiae

<400> SEQUENCE: 39

```
atgtctcaga acgtttacat tgtatcgact gccagaaccc caattggttc attccagggt     60

tctctatcct ccaagacagc agtggaattg ggtgctgttg ctttaaaagg cgccttggct    120

aaggttccag aattggatgc atccaaggat tttgacgaaa ttatttttgg taacgttctt    180

tctgccaatt tgggccaagc tccggccaga caagttgctt tggctgccgg tttgagtaat    240

catatcgttg caagcacagt taacaaggtc tgtgcatccg ctatgaaggc aatcattttg    300

ggtgctcaat ccatcaaatg tggtaatgct gatgttgtcg tagctggtgg ttgtgaatct    360

atgactaacg caccatacta catgccagca gcccgtgcgg gtgccaaatt tggccaaact    420

gttcttgttg atggtgtcga aagagatggg ttgaacgatg cgtacgatgg tctagccatg    480

ggtgtacacg cagaaaagtg tgcccgtgat tgggatatta ctagagaaca acaagacaat    540

tttgccatcg aatcctacca aaaatctcaa aaatctcaaa aggaaggtaa attcgacaat    600

gaaattgtac ctgttaccat taagggattt agaggtaagc ctgatactca agtcacgaag    660

gacgaggaac ctgctagatt acacgttgaa aaattgagat ctgcaaggac tgttttccaa    720

aaagaaaacg gtactgttac tgccgctaac gcttctccaa tcaacgatgg tgctgcagcc    780

gtcatcttgg tttccgaaaa agttttgaag gaaaagaatt tgaagccttt ggctattatc    840

aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agattttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga      1197
```

<210> SEQ ID NO 40
<211> LENGTH: 398
<212> TYPE: PRT
<213> ORGANISM: Saccharomyces cerevisiae

<400> SEQUENCE: 40

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80
```

-continued

```
His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395


<210> SEQ ID NO 41
<211> LENGTH: 1713
<212> TYPE: DNA
<213> ORGANISM: Bacillus subtilis

<400> SEQUENCE: 41

ttgacaaaag caacaaaaga acaaaaatcc cttgtgaaaa acagaggggc ggagcttgtt      60

gttgattgct tagtggagca aggtgtcaca catgtatttg gcattccagg tgcaaaaatt     120

gatgcggtat ttgacgcttt acaagataaa ggacctgaaa ttatcgttgc ccggcacgaa     180

caaaacgcag cattcatggc ccaagcagtc ggccgtttaa ctggaaaacc gggagtcgtg     240

ttagtcacat caggaccggg tgcctctaac ttggcaacag gcctgctgac agcgaacact     300

gaaggagacc ctgtcgttgc gcttgctgga aacgtgatcc gtgcagatcg tttaaaacgg     360
```

```
acacatcaat ctttggataa tgcggcgcta ttccagccga ttacaaaata cagtgtagaa    420

gttcaagatg taaaaaatat accggaagct gttacaaatg catttaggat agcgtcagca    480

gggcaggctg ggccgcttt tgtgagcttt ccgcaagatg ttgtgaatga agtcacaaat     540

acgaaaaacg tgcgtgctgt tgcagcgcca aaactcggtc ctgcagcaga tgatgcaatc    600

agtgcggcca tagcaaaaat ccaaacagca aaacttcctg tcgttttggt cggcatgaaa    660

ggcggaagac cggaagcaat taaagcggtt cgcaagcttt tgaaaaaggt tcagcttcca    720

tttgttgaaa catatcaagc tgccggtacc ctttctagag atttagagga tcaatatttt    780

ggccgtatcg gtttgttccg caaccagcct ggcgatttac tgctagagca ggcagatgtt    840

gttctgacga tcggctatga cccgattgaa tatgatccga aattctggaa tatcaatgga    900

gaccggacaa ttatccattt agacgagatt atcgctgaca ttgatcatgc ttaccagcct    960

gatcttgaat tgatcggtga cattccgtcc acgatcaatc atatcgaaca cgatgctgtg   1020

aaagtggaat ttgcagagcg tgagcagaaa atcctttctg atttaaaaca atatatgcat   1080

gaaggtgagc aggtgcctgc agattggaaa tcagacagag cgcaccctct tgaaatcgtt   1140

aaagagttgc gtaatgcagt cgatgatcat gttacagtaa cttgcgatat cggttcgcac   1200

gccatttgga tgtcacgtta tttccgcagc tacgagccgt taacattaat gatcagtaac   1260

ggtatgcaaa cactcggcgt tgcgcttcct tgggcaatcg gcgcttcatt ggtgaaaccg   1320

ggagaaaaag tggtttctgt ctctggtgac ggcggtttct tattctcagc aatggaatta   1380

gagacagcag ttcgactaaa agcaccaatt gtacacattg tatggaacga cagcacatat   1440

gacatggttg cattccagca attgaaaaaa tataaccgta catctgcggt cgatttcgga   1500

aatatcgata tcgtgaaata tgcggaaagc ttcggagcaa ctggcttgcg cgtagaatca   1560

ccagaccagc tggcagatgt tctgcgtcaa ggcatgaacg ctgaaggtcc tgtcatcatc   1620

gatgtcccgg ttgactacag tgataacatt aatttagcaa gtgacaagct tccgaaagaa   1680

ttcggggaac tcatgaaaac gaaagctctc tag                                1713
```

<210> SEQ ID NO 42
<211> LENGTH: 570
<212> TYPE: PRT
<213> ORGANISM: Bacillus subtilis

<400> SEQUENCE: 42

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
        35                  40                  45

Asp Lys Gly Pro Glu Ile Ile Val Ala Arg His Glu Gln Asn Ala Ala
    50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
```

```
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Ile Asn Gly Asp Arg Thr Ile
    290                 295                 300

Ile His Leu Asp Glu Ile Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
            340                 345                 350

Ser Asp Leu Lys Gln Tyr Met His Glu Gly Glu Gln Val Pro Ala Asp
        355                 360                 365

Trp Lys Ser Asp Arg Ala His Pro Leu Glu Ile Val Lys Glu Leu Arg
    370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
            420                 425                 430

Ile Gly Ala Ser Leu Val Lys Pro Gly Glu Lys Val Val Ser Val Ser
        435                 440                 445

Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Ile Asn Leu Ala Ser Asp Lys Leu Pro Lys Glu
545                 550                 555                 560
```

```
Phe Gly Glu Leu Met Lys Thr Lys Ala Leu
                565                 570


<210> SEQ ID NO 43
<211> LENGTH: 1188
<212> TYPE: DNA
<213> ORGANISM: Saccharomyces cerevisiae

<400> SEQUENCE: 43

atgttgagaa ctcaagccgc cagattgatc tgcaactccc gtgtcatcac tgctaagaga     60

acctttgctt tggccacccg tgctgctgct tacagcagac cagctgcccg tttcgttaag    120

ccaatgatca ctacccgtgg tttgaagcaa atcaacttcg gtggtactgt tgaaaccgtc    180

tacgaaagag ctgactggcc aagagaaaag ttgttggact acttcaagaa cgacactttt    240

gctttgatcg gttacggttc ccaaggttac ggtcaaggtt tgaacttgag agacaacggt    300

ttgaacgtta tcattggtgt ccgtaaagat ggtgcttctt ggaaggctgc catcgaagac    360

ggttgggttc caggcaagaa cttgttcact gttgaagatg ctatcaagag aggtagttac    420

gttatgaact tgttgtccga tgccgctcaa tcagaaacct ggcctgctat caagccattg    480

ttgaccaagg gtaagacttt gtacttctcc cacggtttct ccccagtctt caaggacttg    540

actcacgttg aaccaccaaa ggacttagat gttatcttgg ttgctccaaa gggttccggt    600

agaactgtca gatctttgtt caaggaaggt cgtggtatta actcttctta cgccgtctgg    660

aacgatgtca ccggtaaggc tcacgaaaag gcccaagctt tggccgttgc cattggttcc    720

ggttacgttt accaaaccac tttcgaaaga gaagtcaact ctgacttgta cggtgaaaga    780

ggttgtttaa tgggtggtat ccacggtatg ttcttggctc aatacgacgt cttgagagaa    840

aacggtcact ccccatctga agctttcaac gaaaccgtcg aagaagctac ccaatctcta    900

tacccattga tcggtaagta cggtatggat tacatgtacg atgcttgttc caccaccgcc    960

agaagaggtg ctttggactg gtacccaatc ttcaagaatg ctttgaagcc tgttttccaa   1020

gacttgtacg aatctaccaa gaacggtacc gaaaccaaga gatctttgga attcaactct   1080

caacctgact acagagaaaa gctagaaaag gaattagaca ccatcagaaa catggaaatc   1140

tggaaggttg gtaaggaagt cagaaagttg agaccagaaa accaataa                1188


<210> SEQ ID NO 44
<211> LENGTH: 395
<212> TYPE: PRT
<213> ORGANISM: Saccharomyces cerevisiae

<400> SEQUENCE: 44

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110
```

```
Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395


<210> SEQ ID NO 45
<211> LENGTH: 1029
<212> TYPE: DNA
<213> ORGANISM: Bacillus subtilis

<400> SEQUENCE: 45

atggtaaaag tatattataa cggtgatatc aaagagaacg tattggctgg aaaaacagta      60

gcggttatcg ggtacggttc gcaaggccac gcacatgccc tgaaccttaa agaaagcgga     120

gtagacgtga tcgtcggtgt tagacaagga aaatctttca ctcaagccca agaagacgga     180

cataaagtat tttcagtaaa agaagcggca gcccaagccg aaatcatcat ggttctgctt     240

ccggatgagc agcagcaaaa agtatacgaa gctgaaatca aagatgaatt gacagcagga     300

aaatcattag tattcgctca tggatttaac gtgcatttcc atcaaattgt tcctccggcg     360

gatgtagatg tattcttagt ggcccctaaa ggcccgggac acttggtaag aagaacatat     420

gagcaaggag ctggcgtacc tgcattgttc gcaatctatc aagatgtgac tggagaagca     480

agagacaaag ccctcgctta tgctaaagga atcggcggcg caagagcggg cgtattagaa     540
```

```
acgacattta aagaagaaac agaaacagat ttgttcggtg agcaagcagt tctttgcggc    600

ggattaagcg cgcttgtcaa agccggattt gaaaccttaa ctgaagcagg ttatcagcct    660

gaacttgcat acttcgagtg tcttcatgag ctgaaattaa tcgtagacct tatgtacgaa    720

gaaggacttg caggaatgag atattcaatc tctgacacag cacagtgggg agatttcgta    780

tcaggccctc gcgttgtgga cgccaaagta aaagaatcta tgaaagaagt attaaaagat    840

atccaaaacg gtacattcgc aaaagagtgg atcgtcgaaa accaagtaaa ccgtcctcgt    900

ttcaacgcta tcaatgcaag cgagaacgaa catcaaatcg aagtagtggg aagaaagctt    960

cgtgaaatga tgccgtttgt gaaacaaggc aagaagaagg aagcggtggt ctccgttgcg   1020

caaaattaa                                                           1029
```

```
<210> SEQ ID NO 46
<211> LENGTH: 342
<212> TYPE: PRT
<213> ORGANISM: Bacillus subtilis

<400> SEQUENCE: 46

Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285
```

```
Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Lys Glu Ala Val
                325                 330                 335

Val Ser Val Ala Gln Asn
            340


<210> SEQ ID NO 47
<211> LENGTH: 1758
<212> TYPE: DNA
<213> ORGANISM: Saccharomyces cerevisiae

<400> SEQUENCE: 47

atgggcttgt taacgaaagt tgctacatct agacaattct ctacaacgag atgcgttgca     60

aagaagctca acaagtactc gtatatcatc actgaaccta agggccaagg tgcgtcccag    120

gccatgcttt atgccaccgg tttcaagaag gaagatttca agaagcctca agtcggggtt    180

ggttcctgtt ggtggtccgg taacccatgt aacatgcatc tattggactt gaataacaga    240

tgttctcaat ccattgaaaa agcgggtttg aaagctatgc agttcaacac catcggtgtt    300

tcagacggta tctctatggg tactaaaggt atgagatact cgttacaaag tagagaaatc    360

attgcagact cctttgaaac catcatgatg gcacaacact acgatgctaa catcgccatc    420

ccatcatgtg acaaaaacat gcccggtgtc atgatggcca tgggtagaca taacagacct    480

tccatcatgg tatatggtgg tactatcttg cccggtcatc caacatgtgg ttcttcgaag    540

atctctaaaa acatcgatat cgtctctgcg ttccaatcct acggtgaata tatttccaag    600

caattcactg aagaagaaag agaagatgtt gtggaacatg catgcccagg tcctggttct    660

tgtggtggta tgtatactgc caacacaatg gcttctgccg ctgaagtgct aggtttgacc    720

attccaaact cctcttcctt cccagccgtt tccaaggaga agttagctga gtgtgacaac    780

attggtgaat acatcaagaa gacaatggaa ttgggtattt tacctcgtga tatcctcaca    840

aaagaggctt ttgaaaacgc cattacttat gtcgttgcaa ccggtgggtc cactaatgct    900

gttttgcatt tggtggctgt tgctcactct gcgggtgtca agttgtcacc agatgatttc    960

caaagaatca gtgatactac accattgatc ggtgacttca aaccttctgg taaatacgtc   1020

atggccgatt tgattaacgt tggtggtacc caatctgtga ttaagtatct atatgaaaac   1080

aacatgttgc acggtaacac aatgactgtt accggtgaca ctttggcaga acgtgcaaag   1140

aaagcaccaa gcctacctga aggacaagag attattaagc cactctccca cccaatcaag   1200

gccaacggtc acttgcaaat tctgtacggt tcattggcac caggtggagc tgtgggtaaa   1260

attaccggta aggaaggtac ttacttcaag ggtagagcac gtgtgttcga agaggaaggt   1320

gcctttattg aagccttgga aagaggtgaa atcaagaagg gtgaaaaaac cgttgttgtt   1380

atcagatatg aaggtccaag aggtgcacca ggtatgcctg aaatgctaaa gccttcctct   1440

gctctgatgg gttacggttt gggtaaagat gttgcattgt tgactgatgg tagattctct   1500

ggtggttctc acgggttctt aatcggccac attgttcccg aagccgctga aggtggtcct   1560

atcgggttgg tcagagacgg cgatgagatt atcattgatg ctgataataa caagattgac   1620

ctattagtct ctgataagga aatggctcaa cgtaaacaaa gttgggttgc acctccacct   1680

cgttacacaa gaggtactct atccaagtat gctaagttgg tttccaacgc ttccaacggt   1740

tgtgttttag atgcttga                                                 1758
```

<210> SEQ ID NO 48
<211> LENGTH: 585
<212> TYPE: PRT
<213> ORGANISM: Saccharomyces cerevisiae

<400> SEQUENCE: 48

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
    290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
    370                 375                 380
```

```
Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Glu Gly Ala Phe Ile Glu Ala Leu Glu Arg
        435                 440                 445

Gly Glu Ile Lys Lys Gly Glu Lys Thr Val Val Val Ile Arg Tyr Glu
    450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
    530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585
```

<210> SEQ ID NO 49
<211> LENGTH: 2277
<212> TYPE: DNA
<213> ORGANISM: Saccharomyces cerevisiae

<400> SEQUENCE: 49

```
atggataaca cgaccaatat taatacaaat gagcgctcta gtaacacgga ttttagctca      60

gctcccaata tcaaaggttt gaatagccat actcagttgc agtttgatgc ggattctcga     120

gttttcgttt cggatgtaat ggctaagaac tctaagcaat tattgtacgc ccatatttat     180

aactatttaa tcaaaaacaa ttactggaac tctgccgcaa aatttttaag cgaagctgac     240

cttcctttat ctagaataaa cggatctgct tcgggtggga aactagcttg gaacgccagc     300

ctgaagcagg gattaatgga tattgcatct aagggtgaca ttgttagtga agatgggcta     360

ttaccttcga aaatgctgat ggacgctaat gacacgtttt tactggaatg gtgggaaatt     420

tttcaatcat tgttcaatgg agacctagaa tctgggtacc aacaggatca taatccttta     480

agagagagaa taataccaat tttgccagct aattctaaat ctaatatgcc ttcccatttc     540

tctaatctcc caccaaatgt gattccacca actcaaaata gttttccagt ttcagaggag     600

agttttaggc ccaatggtga cggaagtaac tttaatttaa acgatccaac caatcgaaac     660

gtctccgaaa gatttctatc gagaacttcc ggtgtctacg acaaacagaa tagcgctaat     720

tttgcacctg atactgctat aaacagtgat attgctgggc agcagtacgc aactataaat     780

ctacataaac acttcaatga tttgcaatca ccagcacagc cccagcaatc atctcaacag     840

cagatccagc agcctcagca tcaaccccag catcaaccgc aacagcaaca gcaacagcaa     900

caacaacaac aacaacagca acagcaacag caacagcaac agcagcaaca gcaacagcaa     960

cagcaacaac atcaacagca gcaacagaca ccgtatccta ttgtcaaccc acaaatggtc    1020
```

```
cctcatattc catcggaaaa ttctcattca accggactta tgccttcagt gcctcctaca   1080

aatcaacaat ttaatgcaca aacccaatct tcaatgtttt cagaccagca gcgcttcttt   1140

caatatcaat tacaccacca aaatcaagga caggcgccat cttttcagca aagccaatct   1200

ggcaggtttg atgacatgaa cgctatgaaa atgtttttc agcagcaagc actacagcaa   1260

aattcactac agcaaaatct tggaaatcaa aattatcaat ctaatacacg taacaatact   1320

gcggaagaaa ctacgcccac aaatgacaat aacgcaaatg gcaatagttt attgcaagaa   1380

cacatacgag cccgcttcaa taagatgaaa acaattcctc aacaaatgaa aaatcaaagc   1440

actgtcgcaa atccggttgt tagtgatata acatctcaac agcagtacat gcatatgatg   1500

atgcaaagaa tggcggctaa ccagcaatta caaaatagtg cctttcctcc agacactaat   1560

cgtatagcgc cagctaacaa cactatgcca ttacaaccag gaaatatggg gtctcctgtc   1620

attgaaaatc caggtatgag gcagactaat ccatccggac aaaaccctat gatcaatatg   1680

cagcccttat atcaaaatgt ttcttccgca atgcatgcgt tcgctccgca acaacaattt   1740

catctaccac aacattataa aaccaatact tcagtaccac aaaatgattc tacctccgtc   1800

tttcctttgc ctaacaataa caataacaat aacaacaaca acaataataa taataataat   1860

aatagtaata atagtaataa taataataat aataataata ataataataa tagtaataat   1920

acacccacag tatcacaacc atcatcaaaa tgtacttcta gctccagcac aactcctaat   1980

ataactacaa caattcaacc caagcggaaa cagagagtgg gtaaaacaaa gaccaaggaa   2040

tcaagaaaag ttgctgcagc tcagaaagtt atgaaatcta agaaactgga acaaaatggt   2100

gattcagctg ctacaaactt catcaatgtc actccaaagg acagtggcgg taagggtacc   2160

gtaaaagttc aaaacagtaa ctcgcagcaa caactaaatg gctctttttc tatggataca   2220

gaaacattcg acatatttaa cattggtgac ttttctcctg atctaatgga tagctaa      2277
```

```
<210> SEQ ID NO 50
<211> LENGTH: 758
<212> TYPE: PRT
<213> ORGANISM: Saccharomyces cerevisiae

<400> SEQUENCE: 50

Met Asp Asn Thr Thr Asn Ile Asn Thr Asn Glu Arg Ser Ser Asn Thr
1               5                   10                  15

Asp Phe Ser Ser Ala Pro Asn Ile Lys Gly Leu Asn Ser His Thr Gln
            20                  25                  30

Leu Gln Phe Asp Ala Asp Ser Arg Val Phe Val Ser Asp Val Met Ala
        35                  40                  45

Lys Asn Ser Lys Gln Leu Leu Tyr Ala His Ile Tyr Asn Tyr Leu Ile
    50                  55                  60

Lys Asn Asn Tyr Trp Asn Ser Ala Ala Lys Phe Leu Ser Glu Ala Asp
65                  70                  75                  80

Leu Pro Leu Ser Arg Ile Asn Gly Ser Ala Ser Gly Gly Lys Thr Ser
                85                  90                  95

Leu Asn Ala Ser Leu Lys Gln Gly Leu Met Asp Ile Ala Ser Lys Gly
            100                 105                 110

Asp Ile Val Ser Glu Asp Gly Leu Leu Pro Ser Lys Met Leu Met Asp
        115                 120                 125

Ala Asn Asp Thr Phe Leu Leu Glu Trp Trp Glu Ile Phe Gln Ser Leu
    130                 135                 140

Phe Asn Gly Asp Leu Glu Ser Gly Tyr Gln Gln Asp His Asn Pro Leu
145                 150                 155                 160
```

```
Arg Glu Arg Ile Ile Pro Ile Leu Pro Ala Asn Ser Lys Ser Asn Met
                165                 170                 175

Pro Ser His Phe Ser Asn Leu Pro Pro Asn Val Ile Pro Pro Thr Gln
            180                 185                 190

Asn Ser Phe Pro Val Ser Glu Glu Ser Phe Arg Pro Asn Gly Asp Gly
        195                 200                 205

Ser Asn Phe Asn Leu Asn Asp Pro Thr Asn Arg Asn Val Ser Glu Arg
    210                 215                 220

Phe Leu Ser Arg Thr Ser Gly Val Tyr Asp Lys Gln Asn Ser Ala Asn
225                 230                 235                 240

Phe Ala Pro Asp Thr Ala Ile Asn Ser Asp Ile Ala Gly Gln Gln Tyr
                245                 250                 255

Ala Thr Ile Asn Leu His Lys His Phe Asn Asp Leu Gln Ser Pro Ala
            260                 265                 270

Gln Pro Gln Gln Ser Ser Gln Gln Gln Ile Gln Gln Pro Gln His Gln
        275                 280                 285

Pro Gln His Gln Pro Gln Gln Gln Gln Gln Gln Gln Gln Gln Gln Gln
    290                 295                 300

Gln Gln Gln Gln Gln Gln Gln Gln Gln Gln Gln Gln Gln Gln Gln Gln
305                 310                 315                 320

Gln Gln Gln His Gln Gln Gln Gln Gln Thr Pro Tyr Pro Ile Val Asn
                325                 330                 335

Pro Gln Met Val Pro His Ile Pro Ser Glu Asn Ser His Ser Thr Gly
            340                 345                 350

Leu Met Pro Ser Val Pro Pro Thr Asn Gln Gln Phe Asn Ala Gln Thr
        355                 360                 365

Gln Ser Ser Met Phe Ser Asp Gln Gln Arg Phe Phe Gln Tyr Gln Leu
    370                 375                 380

His His Gln Asn Gln Gly Gln Ala Pro Ser Phe Gln Gln Ser Gln Ser
385                 390                 395                 400

Gly Arg Phe Asp Asp Met Asn Ala Met Lys Met Phe Phe Gln Gln Gln
                405                 410                 415

Ala Leu Gln Gln Asn Ser Leu Gln Gln Asn Leu Gly Asn Gln Asn Tyr
            420                 425                 430

Gln Ser Asn Thr Arg Asn Asn Thr Ala Glu Glu Thr Thr Pro Thr Asn
        435                 440                 445

Asp Asn Asn Ala Asn Gly Asn Ser Leu Leu Gln Glu His Ile Arg Ala
    450                 455                 460

Arg Phe Asn Lys Met Lys Thr Ile Pro Gln Gln Met Lys Asn Gln Ser
465                 470                 475                 480

Thr Val Ala Asn Pro Val Val Ser Asp Ile Thr Ser Gln Gln Gln Tyr
                485                 490                 495

Met His Met Met Met Gln Arg Met Ala Ala Asn Gln Gln Leu Gln Asn
            500                 505                 510

Ser Ala Phe Pro Pro Asp Thr Asn Arg Ile Ala Pro Ala Asn Asn Thr
        515                 520                 525

Met Pro Leu Gln Pro Gly Asn Met Gly Ser Pro Val Ile Glu Asn Pro
    530                 535                 540

Gly Met Arg Gln Thr Asn Pro Ser Gly Gln Asn Pro Met Ile Asn Met
545                 550                 555                 560

Gln Pro Leu Tyr Gln Asn Val Ser Ser Ala Met His Ala Phe Ala Pro
                565                 570                 575

Gln Gln Gln Phe His Leu Pro Gln His Tyr Lys Thr Asn Thr Ser Val
```

```
            580                 585                 590

Pro Gln Asn Asp Ser Thr Ser Val Phe Pro Leu Pro Asn Asn Asn Asn
        595                 600                 605

Asn Asn Asn Asn Asn Asn Asn Asn Asn Asn Asn Asn Asn Ser Asn Asn
    610                 615                 620

Ser Asn Asn Asn Asn Asn Asn Asn Asn Asn Asn Asn Asn Ser Asn Asn
625                 630                 635                 640

Thr Pro Thr Val Ser Gln Pro Ser Ser Lys Cys Thr Ser Ser Ser Ser
                645                 650                 655

Thr Thr Pro Asn Ile Thr Thr Thr Ile Gln Pro Lys Arg Lys Gln Arg
            660                 665                 670

Val Gly Lys Thr Lys Thr Lys Glu Ser Arg Lys Val Ala Ala Ala Gln
        675                 680                 685

Lys Val Met Lys Ser Lys Lys Leu Glu Gln Asn Gly Asp Ser Ala Ala
    690                 695                 700

Thr Asn Phe Ile Asn Val Thr Pro Lys Asp Ser Gly Gly Lys Gly Thr
705                 710                 715                 720

Val Lys Val Gln Asn Ser Asn Ser Gln Gln Gln Leu Asn Gly Ser Phe
                725                 730                 735

Ser Met Asp Thr Glu Thr Phe Asp Ile Phe Asn Ile Gly Asp Phe Ser
            740                 745                 750

Pro Asp Leu Met Asp Ser
        755


<210> SEQ ID NO 51
<211> LENGTH: 2241
<212> TYPE: DNA
<213> ORGANISM: Saccharomyces cerevisiae

<400> SEQUENCE: 51

atggataaca cgaccaatat taatacaaat gagcgctcta gtaacacgga ttttagctca     60

gctcccaata tcaaaggttt gaatagccat actcagttgc agtttgatgc ggattctcga    120

gttttcgttt cggatgcaat ggctaagaac tctaagcaat tattgtacgc ccatatttat    180

aactatttaa gcaaaaacaa ttactggaac tctgccgcaa aatttttaag cgaagctgac    240

cttcctttat ctagaataaa cggatctgct tcgggtgaga aaactagctt gaacgccagc    300

ctgaagcagg gattaatgga tattgcatct aagggtgaca ttgttagtga agatgggcta    360

ttaccttcga aaatgctgat ggacgctaat gacacgtttt tactggaatg gtgggaaatt    420

tttcaatcat tgttcaatgg agacctagaa tctgggtacc aacaggatca taatccttta    480

agagagagaa taataccaat tttgccagct aattctaaat ctaatatgcc ttcccatttc    540

tctaatctcc caccaaatgt gattccacca actcaaaata gttttccagt ttcagaggag    600

agttttaggc ccaatggtga cggtagtaac tttaatttaa acgatccaac caatcgaaac    660

gtctccgaaa gatttctatc gagaacttcc ggtgtctacg acaaacagaa tagcgctaat    720

tttgcacctg atactgctat aaacagtgat attgctgggc agcagtacgc aactataaat    780

ctacataaac acttcaatga tttgcaatca ccagcacagc cccagcaatc atctcaacag    840

cagatccagc agcctcagca tcaaccccag catcaaccgc aacagcaaca acaacaacag    900

caacaacagc aacaacaaca acaacagcaa cagcaacagc aacagcagca acaacagcaa    960

cagcaacaga caccgtatcc tattgtcaac ccacaaatgg tccctcatat tccatcggaa   1020

aattctcatt caaccggact tatgccttca gtgcctccta caaatcaaca atttaatgca   1080

caaacccaat cttcaatgtt ttcagaccag cagcgcttct ttcaatatca attacaccac   1140
```

```
caaaatcaag gacaggcgcc atcttttcag caaagccaat ctggtaggtt tgatgacatg   1200

aacgctatga aaatgttttt tcagcagcaa gcactacagc aaaattcact acagcaaaat   1260

cttggaaatc aaaattatca atctaataca cgtaacaata ctgcggaaga aactacgccc   1320

acaaatgaca ataacgcaaa tggcaatagt ttattgcaag aacacatacg agcccgcttc   1380

aataagatga aaacaattcc tcaacaaatg aaaaatcaaa acactgtcgc aaatccggtt   1440

gttagtgata taacatctca acagcagcac atgcatatga tgatgcaaag aatggcggct   1500

aaccagcaat tacaaaatag tgcctttcct ccagacacta atcgtatagc gccagctaac   1560

aacgctatgc cattacaacc aggaaatatg gggcctcctg tcattgaaaa tccaggtatg   1620

aggcagacta atccatccgg acaaaaccct atgatcaata tgcagccctt atatcaaaat   1680

gtttcttccg caatgcatgc gttcgctccg caacaacaat ttcatctacc acaacattat   1740

aaaaccaata cttcagtacc acaaaatgat tctacctccg tctttccttt gcctaacaat   1800

aacaataaca ataacaataa caacaacaat aataataata gtaataatag taataacaat   1860

aataataata ataatagtaa taatacaccc acagtatcac aaccatcatc aaaacgtact   1920

tctagctcca gcacaactcc taatataact acaaccattc aacccaagcg gaaacagaga   1980

gtgggtaaaa caaagaccaa ggaatcaaga aaagttgctg ccgctcagaa agttatgaaa   2040

tctaagaaac tggaacaaaa tggtgattca gctgctacaa acttcatcaa tgtcactcca   2100

aaggacagtg gcggtaaggg taccgtaaaa gttcaaaaca gtaactcgca gcaacaacta   2160

aatggctctt tttctatgga tacagaaaca ttcgacatat ttaacattgg tgacttttct   2220

cctgatctaa tggatagcta a                                             2241
```

<210> SEQ ID NO 52
<211> LENGTH: 746
<212> TYPE: PRT
<213> ORGANISM: Saccharomyces cerevisiae

<400> SEQUENCE: 52

```
Met Asp Asn Thr Thr Asn Ile Asn Thr Asn Glu Arg Ser Ser Asn Thr
1               5                   10                  15

Asp Phe Ser Ser Ala Pro Asn Ile Lys Gly Leu Asn Ser His Thr Gln
            20                  25                  30

Leu Gln Phe Asp Ala Asp Ser Arg Val Phe Val Ser Asp Ala Met Ala
        35                  40                  45

Lys Asn Ser Lys Gln Leu Leu Tyr Ala His Ile Tyr Asn Tyr Leu Ser
    50                  55                  60

Lys Asn Asn Tyr Trp Asn Ser Ala Ala Lys Phe Leu Ser Glu Ala Asp
65                  70                  75                  80

Leu Pro Leu Ser Arg Ile Asn Gly Ser Ala Ser Gly Glu Lys Thr Ser
                85                  90                  95

Leu Asn Ala Ser Leu Lys Gln Gly Leu Met Asp Ile Ala Ser Lys Gly
            100                 105                 110

Asp Ile Val Ser Glu Asp Gly Leu Leu Pro Ser Lys Met Leu Met Asp
        115                 120                 125

Ala Asn Asp Thr Phe Leu Leu Glu Trp Trp Glu Ile Phe Gln Ser Leu
    130                 135                 140

Phe Asn Gly Asp Leu Glu Ser Gly Tyr Gln Gln Asp His Asn Pro Leu
145                 150                 155                 160

Arg Glu Arg Ile Ile Pro Ile Leu Pro Ala Asn Ser Lys Ser Asn Met
                165                 170                 175
```

```
Pro Ser His Phe Ser Asn Leu Pro Pro Asn Val Ile Pro Pro Thr Gln
            180                 185                 190

Asn Ser Phe Pro Val Ser Glu Glu Ser Phe Arg Pro Asn Gly Asp Gly
        195                 200                 205

Ser Asn Phe Asn Leu Asn Asp Pro Thr Asn Arg Asn Val Ser Glu Arg
    210                 215                 220

Phe Leu Ser Arg Thr Ser Gly Val Tyr Asp Lys Gln Asn Ser Ala Asn
225                 230                 235                 240

Phe Ala Pro Asp Thr Ala Ile Asn Ser Asp Ile Ala Gly Gln Gln Tyr
                245                 250                 255

Ala Thr Ile Asn Leu His Lys His Phe Asn Asp Leu Gln Ser Pro Ala
            260                 265                 270

Gln Pro Gln Gln Ser Ser Gln Gln Gln Ile Gln Gln Pro Gln His Gln
        275                 280                 285

Pro Gln His Gln Pro Gln Gln Gln Gln Gln Gln Gln Gln Gln Gln Gln
    290                 295                 300

Gln Gln Gln Gln Gln Gln Gln Gln Gln Gln Gln Gln Gln Gln Gln Gln
305                 310                 315                 320

Gln Gln Gln Thr Pro Tyr Pro Ile Val Asn Pro Gln Met Val Pro His
                325                 330                 335

Ile Pro Ser Glu Asn Ser His Ser Thr Gly Leu Met Pro Ser Val Pro
            340                 345                 350

Pro Thr Asn Gln Gln Phe Asn Ala Gln Thr Gln Ser Ser Met Phe Ser
        355                 360                 365

Asp Gln Gln Arg Phe Phe Gln Tyr Gln Leu His His Gln Asn Gln Gly
    370                 375                 380

Gln Ala Pro Ser Phe Gln Gln Ser Gln Ser Gly Arg Phe Asp Asp Met
385                 390                 395                 400

Asn Ala Met Lys Met Phe Phe Gln Gln Gln Ala Leu Gln Gln Asn Ser
                405                 410                 415

Leu Gln Gln Asn Leu Gly Asn Gln Asn Tyr Gln Ser Asn Thr Arg Asn
            420                 425                 430

Asn Thr Ala Glu Glu Thr Thr Pro Thr Asn Asp Asn Asn Ala Asn Gly
        435                 440                 445

Asn Ser Leu Leu Gln Glu His Ile Arg Ala Arg Phe Asn Lys Met Lys
    450                 455                 460

Thr Ile Pro Gln Gln Met Lys Asn Gln Asn Thr Val Ala Asn Pro Val
465                 470                 475                 480

Val Ser Asp Ile Thr Ser Gln Gln Gln His Met His Met Met Met Gln
                485                 490                 495

Arg Met Ala Ala Asn Gln Gln Leu Gln Asn Ser Ala Phe Pro Pro Asp
            500                 505                 510

Thr Asn Arg Ile Ala Pro Ala Asn Asn Ala Met Pro Leu Gln Pro Gly
        515                 520                 525

Asn Met Gly Pro Pro Val Ile Glu Asn Pro Gly Met Arg Gln Thr Asn
    530                 535                 540

Pro Ser Gly Gln Asn Pro Met Ile Asn Met Gln Pro Leu Tyr Gln Asn
545                 550                 555                 560

Val Ser Ser Ala Met His Ala Phe Ala Pro Gln Gln Gln Phe His Leu
                565                 570                 575

Pro Gln His Tyr Lys Thr Asn Thr Ser Val Pro Gln Asn Asp Ser Thr
            580                 585                 590

Ser Val Phe Pro Leu Pro Asn Asn Asn Asn Asn Asn Asn Asn Asn Asn
        595                 600                 605
```

```
Asn Asn Asn Asn Asn Ser Asn Asn Ser Asn Asn Asn Asn Asn Asn Asn
    610                 615                 620

Asn Ser Asn Asn Thr Pro Thr Val Ser Gln Pro Ser Ser Lys Arg Thr
625                 630                 635                 640

Ser Ser Ser Ser Thr Thr Pro Asn Ile Thr Thr Thr Ile Gln Pro Lys
                645                 650                 655

Arg Lys Gln Arg Val Gly Lys Thr Lys Thr Lys Glu Ser Arg Lys Val
            660                 665                 670

Ala Ala Ala Gln Lys Val Met Lys Ser Lys Lys Leu Glu Gln Asn Gly
        675                 680                 685

Asp Ser Ala Ala Thr Asn Phe Ile Asn Val Thr Pro Lys Asp Ser Gly
    690                 695                 700

Gly Lys Gly Thr Val Lys Val Gln Asn Ser Asn Ser Gln Gln Gln Leu
705                 710                 715                 720

Asn Gly Ser Phe Ser Met Asp Thr Glu Thr Phe Asp Ile Phe Asn Ile
                725                 730                 735

Gly Asp Phe Ser Pro Asp Leu Met Asp Ser
            740                 745
```

<210> SEQ ID NO 53
<211> LENGTH: 2238
<212> TYPE: DNA
<213> ORGANISM: Saccharomyces cerevisiae

<400> SEQUENCE: 53

```
atggataaca cgaccaatat taatacaaat gagcgctcta gtaacacgga ttttagctca     60

gctcccaata tcaaaggttt gaatagccat actcagttgc agtttgatgc ggattctcga    120

gttttcgttt cggatgcaat ggctaagaac tctaagcaat tattgtacgc ccatatttat    180

aactatttaa gcaaaaacaa ttactggaac tctgccgcaa aatttttaag cgaagctgac    240

cttcctttat ctagaataaa cggatctgct tcgggtgaga aaactagctt gaacgccagc    300

ctgaagcagg gattaatgga tattgcatct aagggtgaca ttgttagtga agatgggcta    360

ttaccttcga aaatgctgat ggacgctaat gacacgtttt tactggaatg gtgggaaatt    420

tttcaatcat tgttcaatgg agacctagaa tctgggtacc aacaggatca taatccttta    480

agagagagaa taataccaat tttgccagct aattctaaat ctaatatgcc ttcccatttc    540

tctaatctcc caccaaatgt gattccacca actcaaaata gttttccagt ttcagaggag    600

agttttaggc ccaatggtga cggtagtaac tttaatttaa acgatccaac caatcgaaac    660

gtctccgaaa gatttctatc gagaacttcc ggtgtctacg acaaacagaa tagcgctaat    720

tttgcacctg atactgctat aaatagtgat attgctgggc agcagtacgc aactataaat    780

ctacataaac acttcaatga tttgcaatca ccagcacagc cccagcaatc atctcaacag    840

cagatccagc agcctcagca tcaaccccag catcaaccgc aacagcaacc gcaacagcaa    900

caacaacaac agcaacaaca gcaacaacaa caacaacagc aacagcaaca gcaacagcag    960

caacaacagc agcaacagca gcaacaacag caacagcaac agacaccgta tcctattgtc   1020

aacccacaaa tggtccctca tattccatcg gaaaattctc attcaaccgg acttatgcct   1080

tcagtgcctc ctacaaatca acaatttaat gcacaaaccc aatcttcaat gttttcagac   1140

cagcagcgct tctttcaata tcaattacac caccaaaatc aaggacaggc gccatctttt   1200

cagcaaagcc aatctggtag gtttgatgac atgaacgcta tgaaaatgtt ttttcagcag   1260

caagcactac agcaaaattc actacagcaa aatcttggaa atcaaaatta tcaatctaat   1320
```

```
acacgtaaca atactgcgga agaaactacg cccacaaatg acaataacgc aaatggcaat   1380

agtttattgc aagaacacat acgagcccgc ttcaataaga tgaaaacaat tcctcaacaa   1440

atgaaaaatc aaaacactgt cgcaaatccg gttgttagtg atataacatc tcaacagcag   1500

tacatgcata tgatgatgca aagaatggcg gctaaccagc aattacaaaa tagtgccttt   1560

cctccagaca ctaatcgtat agcgccagct aacaacgcta tgccattaca accaggaaat   1620

atggggcctc ctgtcattga aaatccaggt atgaggcaga ctaatccatc cggacaaaac   1680

cctatgatca atatgcagcc cttatatcaa aatgtttctt ccgcaatgca tgcgttcgct   1740

ccgcaacaac aatttcatct accacaacat tataaaacca atacttcagt accacaaaat   1800

gattctacct ccgtctttcc tttgcctaac aataacaata acaataacaa taacaacaac   1860

aataataata atagtaataa tagtaataac aataataata ataataatag taataataca   1920

cccacagtat cacaaccatc atcaaaacgt acttctagct ccagcacaac tcctaatata   1980

actacaacca ttcaacccaa gcggaaacag agagtgggta aaacaaagac caaggaatca   2040

agaaaagttg ctgccgctca gaaagttatg aaatctaaga aactggaaca aaatggtgat   2100

tcagctgcta caaacttcat caatgtcact ccaaaggaca gtggcggtaa gggtaccgta   2160

aaagttcaaa acagtaactc gcagcaacaa ctaaaatggc tctttttcta tggatacaga   2220

aacattcgac atatttaa                                                 2238
```

<210> SEQ ID NO 54
<211> LENGTH: 745
<212> TYPE: PRT
<213> ORGANISM: Saccharomyces cerevisiae

<400> SEQUENCE: 54

```
Met Asp Asn Thr Thr Asn Ile Asn Thr Asn Glu Arg Ser Ser Asn Thr
1               5                   10                  15

Asp Phe Ser Ser Ala Pro Asn Ile Lys Gly Leu Asn Ser His Thr Gln
            20                  25                  30

Leu Gln Phe Asp Ala Asp Ser Arg Val Phe Val Ser Asp Ala Met Ala
        35                  40                  45

Lys Asn Ser Lys Gln Leu Leu Tyr Ala His Ile Tyr Asn Tyr Leu Ser
    50                  55                  60

Lys Asn Asn Tyr Trp Asn Ser Ala Ala Lys Phe Leu Ser Glu Ala Asp
65                  70                  75                  80

Leu Pro Leu Ser Arg Ile Asn Gly Ser Ala Ser Gly Glu Lys Thr Ser
                85                  90                  95

Leu Asn Ala Ser Leu Lys Gln Gly Leu Met Asp Ile Ala Ser Lys Gly
            100                 105                 110

Asp Ile Val Ser Glu Asp Gly Leu Leu Pro Ser Lys Met Leu Met Asp
        115                 120                 125

Ala Asn Asp Thr Phe Leu Leu Glu Trp Trp Glu Ile Phe Gln Ser Leu
    130                 135                 140

Phe Asn Gly Asp Leu Glu Ser Gly Tyr Gln Gln Asp His Asn Pro Leu
145                 150                 155                 160

Arg Glu Arg Ile Ile Pro Ile Leu Pro Ala Asn Ser Lys Ser Asn Met
                165                 170                 175

Pro Ser His Phe Ser Asn Leu Pro Pro Asn Val Ile Pro Pro Thr Gln
            180                 185                 190

Asn Ser Phe Pro Val Ser Glu Glu Ser Phe Arg Pro Asn Gly Asp Gly
        195                 200                 205

Ser Asn Phe Asn Leu Asn Asp Pro Thr Asn Arg Asn Val Ser Glu Arg
```

```
    210                 215                 220

Phe Leu Ser Arg Thr Ser Gly Val Tyr Asp Lys Gln Asn Ser Ala Asn
225                 230                 235                 240

Phe Ala Pro Asp Thr Ala Ile Asn Ser Asp Ile Ala Gly Gln Gln Tyr
                245                 250                 255

Ala Thr Ile Asn Leu His Lys His Phe Asn Asp Leu Gln Ser Pro Ala
            260                 265                 270

Gln Pro Gln Gln Ser Ser Gln Gln Gln Ile Gln Gln Pro Gln His Gln
        275                 280                 285

Pro Gln His Gln Pro Gln Gln Gln Pro Gln Gln Gln Gln Gln Gln Gln
    290                 295                 300

Gln Gln Gln Gln Gln Gln Gln Gln Gln Gln Gln Gln Gln Gln Gln Gln
305                 310                 315                 320

Gln Gln Gln Gln Gln Gln Gln Gln Gln Gln Gln Gln Gln Gln Thr Pro
                325                 330                 335

Tyr Pro Ile Val Asn Pro Gln Met Val Pro His Ile Pro Ser Glu Asn
            340                 345                 350

Ser His Ser Thr Gly Leu Met Pro Ser Val Pro Pro Thr Asn Gln Gln
        355                 360                 365

Phe Asn Ala Gln Thr Gln Ser Ser Met Phe Ser Asp Gln Gln Arg Phe
    370                 375                 380

Phe Gln Tyr Gln Leu His His Gln Asn Gln Gly Gln Ala Pro Ser Phe
385                 390                 395                 400

Gln Gln Ser Gln Ser Gly Arg Phe Asp Asp Met Asn Ala Met Lys Met
                405                 410                 415

Phe Phe Gln Gln Ala Leu Gln Gln Asn Ser Leu Gln Gln Asn Leu
            420                 425                 430

Gly Asn Gln Asn Tyr Gln Ser Asn Thr Arg Asn Asn Thr Ala Glu Glu
        435                 440                 445

Thr Thr Pro Thr Asn Asp Asn Asn Ala Asn Gly Asn Ser Leu Leu Gln
    450                 455                 460

Glu His Ile Arg Ala Arg Phe Asn Lys Met Lys Thr Ile Pro Gln Gln
465                 470                 475                 480

Met Lys Asn Gln Asn Thr Val Ala Asn Pro Val Val Ser Asp Ile Thr
                485                 490                 495

Ser Gln Gln Gln Tyr Met His Met Met Met Gln Arg Met Ala Ala Asn
            500                 505                 510

Gln Gln Leu Gln Asn Ser Ala Phe Pro Pro Asp Thr Asn Arg Ile Ala
        515                 520                 525

Pro Ala Asn Asn Ala Met Pro Leu Gln Pro Gly Asn Met Gly Pro Pro
    530                 535                 540

Val Ile Glu Asn Pro Gly Met Arg Gln Thr Asn Pro Ser Gly Gln Asn
545                 550                 555                 560

Pro Met Ile Asn Met Gln Pro Leu Tyr Gln Asn Val Ser Ser Ala Met
                565                 570                 575

His Ala Phe Ala Pro Gln Gln Gln Phe His Leu Pro Gln His Tyr Lys
            580                 585                 590

Thr Asn Thr Ser Val Pro Gln Asn Asp Ser Thr Ser Val Phe Pro Leu
        595                 600                 605

Pro Asn Asn Asn Asn Asn Asn Asn Asn Asn Asn Asn Asn Asn Asn Asn
    610                 615                 620

Ser Asn Asn Ser Asn Asn Asn Asn Asn Asn Asn Asn Ser Asn Asn Thr
625                 630                 635                 640
```

```
Pro Thr Val Ser Gln Pro Ser Ser Lys Arg Thr Ser Ser Ser Ser Thr
                645                 650                 655

Thr Pro Asn Ile Thr Thr Thr Ile Gln Pro Lys Arg Lys Gln Arg Val
            660                 665                 670

Gly Lys Thr Lys Thr Lys Glu Ser Arg Lys Val Ala Ala Ala Gln Lys
        675                 680                 685

Val Met Lys Ser Lys Lys Leu Glu Gln Asn Gly Asp Ser Ala Ala Thr
    690                 695                 700

Asn Phe Ile Asn Val Thr Pro Lys Asp Ser Gly Gly Lys Gly Thr Val
705                 710                 715                 720

Lys Val Gln Asn Ser Asn Ser Gln Gln Gln Leu Lys Trp Leu Phe Phe
                725                 730                 735

Tyr Gly Tyr Arg Asn Ile Arg His Ile
            740                 745


<210> SEQ ID NO 55
<211> LENGTH: 23
<212> TYPE: DNA
<213> ORGANISM: artificial sequence
<220> FEATURE:
<223> OTHER INFORMATION: primer

<400> SEQUENCE: 55

ctatgcgcac ccgttctcgg agc                                            23


<210> SEQ ID NO 56
<211> LENGTH: 22
<212> TYPE: DNA
<213> ORGANISM: artificial sequence
<220> FEATURE:
<223> OTHER INFORMATION: primer

<400> SEQUENCE: 56

cgctcatgag cccgaagtgg cg                                             22


<210> SEQ ID NO 57
<211> LENGTH: 22
<212> TYPE: DNA
<213> ORGANISM: artificial sequence
<220> FEATURE:
<223> OTHER INFORMATION: primer

<400> SEQUENCE: 57

ggtatctccc ggatcctttg tc                                             22


<210> SEQ ID NO 58
<211> LENGTH: 22
<212> TYPE: DNA
<213> ORGANISM: artificial sequence
<220> FEATURE:
<223> OTHER INFORMATION: primer

<400> SEQUENCE: 58

cgctcatgag cccgaagtgg cg                                             22


<210> SEQ ID NO 59
<211> LENGTH: 34
<212> TYPE: DNA
<213> ORGANISM: artificial sequence
<220> FEATURE:
<223> OTHER INFORMATION: primer

<400> SEQUENCE: 59

aaggagtact tgtttttaga atatacggtc aacg                                34
```

<210> SEQ ID NO 60
<211> LENGTH: 30
<212> TYPE: DNA
<213> ORGANISM: artificial sequence
<220> FEATURE:
<223> OTHER INFORMATION: primer

<400> SEQUENCE: 60
gatggaatat gagggaccat ttgtgggttg 30

<210> SEQ ID NO 61
<211> LENGTH: 43
<212> TYPE: DNA
<213> ORGANISM: artificial sequence
<220> FEATURE:
<223> OTHER INFORMATION: primer

<400> SEQUENCE: 61
ccgctgctag gcgcgccgtg tctgaaaacg gaagaggagt agg 43

<210> SEQ ID NO 62
<211> LENGTH: 44
<212> TYPE: DNA
<213> ORGANISM: artificial sequence
<220> FEATURE:
<223> OTHER INFORMATION: primer

<400> SEQUENCE: 62
gcagggatgc ggccgctgac ataacagaca tactccaagc tgcc 44

<210> SEQ ID NO 63
<211> LENGTH: 45
<212> TYPE: DNA
<213> ORGANISM: artificial sequence
<220> FEATURE:
<223> OTHER INFORMATION: primer

<400> SEQUENCE: 63
ccgctgctag gcgcgccgtg catttggctt tttgattgat tgtac 45

<210> SEQ ID NO 64
<211> LENGTH: 47
<212> TYPE: DNA
<213> ORGANISM: artificial sequence
<220> FEATURE:
<223> OTHER INFORMATION: primer

<400> SEQUENCE: 64
gcagggatgc ggccgctgac acttttattt tctctttttg cactcct 47

<210> SEQ ID NO 65
<211> LENGTH: 20
<212> TYPE: DNA
<213> ORGANISM: artificial sequence
<220> FEATURE:
<223> OTHER INFORMATION: primer

<400> SEQUENCE: 65
ccgctgctag gcgcgccgtg 20

<210> SEQ ID NO 66
<211> LENGTH: 25
<212> TYPE: DNA
<213> ORGANISM: artificial sequence
<220> FEATURE:
<223> OTHER INFORMATION: primer

<400> SEQUENCE: 66
gagcaatgaa cccaataacg aaatc 25

<210> SEQ ID NO 67
<211> LENGTH: 20
<212> TYPE: DNA
<213> ORGANISM: artificial sequence
<220> FEATURE:
<223> OTHER INFORMATION: primer

<400> SEQUENCE: 67
gcagggatgc ggccgctgac 20

<210> SEQ ID NO 68
<211> LENGTH: 25
<212> TYPE: DNA
<213> ORGANISM: artificial sequence
<220> FEATURE:
<223> OTHER INFORMATION: primer

<400> SEQUENCE: 68
cttgacgttc gttcgactga tgagc 25

<210> SEQ ID NO 69
<211> LENGTH: 448
<212> TYPE: DNA
<213> ORGANISM: Saccharomyces cerevisiae

<400> SEQUENCE: 69
cccattaccg acatttgggc gctatacgtg catatgttca tgtatgtatc tgtatttaaa 60
acacttttgt attatttttc ctcatatatg tgtataggtt tatacggatg atttaattat 120
tacttcacca ccctttattt caggctgata tcttagcctt gttactagtt agaaaaagac 180
atttttgctg tcagtcactg tcaagagatt cttttgctgg catttcttct agaagcaaaa 240
agagcgatgc gtcttttccg ctgaaccgtt ccagcaaaaa agactaccaa cgcaatatgg 300
attgtcagaa tcatataaaa gagaagcaaa taactccttg tcttgtatca attgcattat 360
aatatcttct tgttagtgca atatcatata gaagtcatcg aaatagatat taagaaaaac 420
aaactgtaca atcaatcaat caatcatc 448

<210> SEQ ID NO 70
<211> LENGTH: 270
<212> TYPE: DNA
<213> ORGANISM: Saccharomyces cerevisiae

<400> SEQUENCE: 70
gacctcgagt catgtaatta gttatgtcac gcttacattc acgccctccc cccacatccg 60
ctctaaccga aaaggaagga gttagacaac ctgaagtcta ggtccctatt tattttttta 120
tagttatgtt agtattaaga acgttattta tatttcaaat ttttcttttt tttctgtaca 180
gacgcgtgta cgcatgtaac attatactga aaaccttgct tgagaaggtt ttgggacgct 240
cgaaggcttt aatttgcggc cggtacccaa 270

<210> SEQ ID NO 71
<211> LENGTH: 643
<212> TYPE: DNA
<213> ORGANISM: Saccharomyces cerevisiae

<400> SEQUENCE: 71
gaaatgaata acaatactga cagtactaaa taattgccta cttggcttca catacgttgc 60

```
atacgtcgat atagataata atgataatga cagcaggatt atcgtaatac gtaatagttg    120

aaaatctcaa aaatgtgtgg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360

tctgttctct tctgactttg actcctcaaa aaaaaaaaat ctacaatcaa cagatcgctt    420

caattacgcc ctcacaaaaa ctttttttcct tcttcttcgc ccacgttaaa ttttatccct    480

catgttgtct aacggatttc tgcacttgat ttattataaa aagacaaaga cataatactt    540

ctctatcaat ttcagttatt gttcttcctt gcgttattct tctgttcttc tttttctttt    600

gtcatatata accataacca agtaatacat attcaaatct aga                      643
```

<210> SEQ ID NO 72
<211> LENGTH: 316
<212> TYPE: DNA
<213> ORGANISM: Saccharomyces cerevisiae

<400> SEQUENCE: 72

```
gagtaagcga atttcttatg atttatgatt tttattatta aataagttat aaaaaaaata     60

agtgtataca aattttaaag tgactcttag gttttaaaac gaaaattctt attcttgagt    120

aactctttcc tgtaggtcag gttgctttct caggtatagc atgaggtcgc tcttattgac    180

cacacctcta ccggcatgcc gagcaaatgc ctgcaaatcg ctccccattt cacccaattg    240

tagatatgct aactccagca atgagttgat gaatctcggt gtgtatttta tgtcctcaga    300

ggacaacacc tgtggt                                                    316
```

<210> SEQ ID NO 73
<211> LENGTH: 753
<212> TYPE: DNA
<213> ORGANISM: Saccharomyces cerevisiae

<400> SEQUENCE: 73

```
gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatagccata    300

gtgatgtcta agtaaccttt atggtatatt tcttaatgtg gaaagatact agcgcgcgca    360

cccacacaca agcttcgtct tttcttgaag aaaagaggaa gctcgctaaa tgggattcca    420

ctttccgttc cctgccagct gatggaaaaa ggttagtgga acgatgaaga ataaaaagag    480

agatccactg aggtgaaatt tcagctgaca gcgagtttca tgatcgtgat gaacaatggt    540

aacgagttgt ggctgttgcc agggagggtg gttctcaact tttaatgtat ggccaaatcg    600

ctacttgggt ttgttatata acaaagaaga aataatgaac tgattctctt cctccttctt    660

gtcctttctt aattctgttg taattacctt cctttgtaat tttttttgta attattcttc    720

ttaataatcc aaacaaacac acatattaca ata                                 753
```

YEAST WITH INCREASED BUTANOL TOLERANCE INVOLVING FILAMENTOUS GROWTH RESPONSE

CROSS REFERENCE TO RELATED APPLICATIONS

This application is related to and claims the benefit of priority of U.S. Provisional Patent Application No. 61/141,013, filed Dec. 29, 2008, the entirety of which is herein incorporated by reference.

FIELD OF THE INVENTION

The invention relates to the field of microbiology and genetic engineering. More specifically, yeast genes that are involved in the cell response to butanol were identified. These genes may be engineered to improve growth yield in the presence of butanol.

BACKGROUND OF THE INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Butanol may be made through chemical synthesis or by fermentation. Isobutanol is produced biologically as a by-product of yeast fermentation. It is a component of "fusel oil" that forms as a result of incomplete metabolism of amino acids by this group of fungi. Isobutanol is specifically produced from catabolism of L-valine and the yield is typically very low. Additionally, recombinant microbial production hosts, expressing a 1-butanol biosynthetic pathway (Donaldson et al., U.S. Patent Application Publication No. US20080182308A1), a 2-butanol biosynthetic pathway (Donaldson et al., U.S. Patent Publication Nos. US 20070259410A1 and US 20070292927), and an isobutanol biosynthetic pathway (Maggio-Hall et al., U.S. Patent Publication No. US 20070092957) have been described.

Biological production of butanols is believed to be limited by butanol toxicity to the host microorganism used in fermentation for butanol production. Yeast are typically sensitive to butanol in the medium. Using a screen for 1-butanol insensitive *Saccharomyces cerevisiae* mutants, Lorenz et al. (Molec. Biol. of the Cell (2000) 11:183-199) identified proteins that regulate polarized growth (BUD8, BEM1, BEM4, and FIG1), mitochondrial function (MSM1, MRP21, and HM11), and a transcriptional regulator (CHD1). They also found that 1-butanol stimulates filamentous growth in haploid cells and induces cell elongation and changes in budding pattern, leading to a pseudohyphal morphology. Ashe et al. (The EMBO Journal (2001) 20:6464-6474) found that butanol brings about a rapid inhibition of translation at the initiation step in *Saccharomyces cerevisiae*. The GCD1-P180 allele has a single amino acid change in Gcd1p, which is part of the eIF2B guanine nucleotide complex that is responsible for recycling eIF2-GDP to eIF2-GTP, that allows translational regulation upon butanol addition. Smirnova et al. (Molecular and Cellular Bioloty (2005) 25:9340-9340) found by using microarray analysis that with addition of fusel alcohol, there is widespread translational reprogramming in yeast. These studies all indicate the complexity of butanol sensitivity in yeast.

*S. cerevisiae* responds to the presence of fusel alcohols and to limitation of carbon or nitrogen with filamentous growth, which is also described as pseudohyphae formation or invasive growth (da Silva et al. (2007) World J. of Microbiol. and Biotech. 23:697-704); Dickinson (2008) Folia Microbiol. (Praha) 53:3-14). Nearly 500 genes have been identified that affect filamentous growth (Jin et al. (2008) Molec. Biol. of the Cell 19:284-296). Several genes are implicated in the fusel alcohol-induced formation of pseudohyphae, and experimental evidence indicates that fusel alcohol-induced pseudohyphae arise in an entirely different way from pseudohyphae induced by nitrogen-limited growth (Martinez-Anaya et al. (2003) J. of Cell Science 116:3423-3431; Vancetto and Ceccato-Antonini (2007) J. Applied Micro. And Biotech. 75:111-115). Specifically, MUC1 (also designated FLO11) and MSS11 are essential for filamentous growth induced by nitrogen starvation but are not required for butanol-induced filamentous growth (Lorenz et al. (2000) Mol. Biol. Cell. 11:183-199).

There remains a need for yeast cells with increased tolerance to butanol, as well as methods of producing butanols using yeast host strains that are more tolerant to these chemicals. To this end applicants have Identified genes in yeast that are involved in butanol tolerance, that can be engineered to increase the level of butanol tolerance in yeast cells used for butanol production.

SUMMARY OF THE INVENTION

Provided herein are recombinant yeast cells comprising: a) a butanol biosynthetic pathway; and b) at least one genetic modification which increases activity of the nitrogen starvation-induced filamentous growth response; wherein the butanol biosynthetic pathway comprises at least one gene that is heterologous to the yeast cell and wherein the yeast cell has an increase in tolerance to butanol as compared with a yeast cell that lacks the at least one genetic modification of (b).

In some embodiments, the cell has at least about a 2-fold increase in doubling time in 1.5% (w/v) isobutanol as compared to a parental cell having no increase in activity of the nitrogen starvation-induced filamentous growth response. In some embodiments, the yeast is selected from the group consisting of *Saccharomyces, Schizosaccharomyces, Hansenula, Candida, Kluyveromyces, Yarrowia* and *Pichia*. In some embodiments, the genetic modification increases response to a pathway selected from the group consisting of the Target of Rapamycin pathway, cAMP-PKA pathway, mitogen-activated protein kinase module of the nitrogen starvation-induced filamentous growth response, and glucose repression signal pathway. In some embodiments, the genetic modification increases MSS11p activity. In some embodiments, the modification increasing MSS11p activity is overexpression of an MSS11 protein encoding gene. In some embodiments, the MSS11 protein encoding gene encodes a protein having an amino acid sequence with at least about 90% sequence identity to a sequence selected from the group consisting of SEQ ID NOs:50, 52, and 54 based on Clustal W method of alignment using the default parameters of GAP PENALTY=10, GAP LENGTH PENALTY=0.1, and Gonnet 250 series of protein weight matrix. In some embodiments, the genetic modification increasing the MSS11p activity is the overexpression of a gene selected from the group consisting of TAP42, SIT4, PHP21, PNP22, MEP2, GPR1, GPB1, GPB2, CYR1, BCY1, RAS, TPK1, TPK2, SFL1, HDA1, FLOG, MEP2, STE11, STE7, KSS1, STE12, TEC1, MSB2, CDC42, SHO1, STE20, IRA1, IRA2, SNF1, SNF4, SIP1, TUP1, SSN6, MIG1, and NRG1.

Also provided is a recombinant yeast cell comprising a heterologous MSS11 protein encoding gene and a butanol biosynthetic pathway. In some embodiments, the butanol biosynthetic pathway comprises at least one gene that is heterologous to the yeast cell. In some embodiments, the yeast cell has an increased tolerance to butanol as compared to a yeast cell that does not comprise at least one heterologous MSS11 protein encoding gene.

In some embodiments, the butanol biosynthetic pathway is selected from the group consisting of: a) a 1-butanol biosynthetic pathway; b) a 2-butanol biosynthetic pathway; and c) an isobutanol biosynthetic pathway. In some embodiments, the 1-butanol biosynthetic pathway comprises at least one gene encoding a polypeptide that performs at least one of the following substrate to product conversions: a) acetyl-CoA to acetoacetyl-CoA, as catalyzed by acetyl-CoA acetyltransferase; b) acetoacetyl-CoA to 3-hydroxybutyryl-CoA, as catalyzed by 3-hydroxybutyryl-CoA dehydrogenase; c) 3-hydroxybutyryl-CoA to crotonyl-CoA, as catalyzed by crotonase; d) crotonyl-CoA to butyryl-CoA, as catalyzed by butyryl-CoA dehydrogenase; e) butyryl-CoA to butyraldehyde, as catalyzed by butyraldehyde dehydrogenase; and f) butyraldehyde to 1-butanol, as catalyzed by 1-butanol dehydrogenase. In some embodiments, the 2-butanol biosynthetic pathway comprises at least one gene encoding a polypeptide that performs at least one of the following substrate to product conversions: a) pyruvate to alpha-acetolactate, as catalyzed by acetolactate synthase; b) alpha-acetolactate to acetoin, as catalyzed by acetolactate decarboxylase; c) acetoin to 2,3-butanediol, as catalyzed by butanediol dehydrogenase; d) 2,3-butanediol to 2-butanone, as catalyzed by butanediol dehydratase; and e) 2-butanone to 2-butanol, as catalyzed by 2-butanol dehydrogenase. In some embodiments, the isobutanol biosynthetic pathway comprises at least one gene encoding a polypeptide that performs at least one of the following substrate to product conversions: a) pyruvate to acetolactate, as catalyzed by acetolactate synthase; b) acetolactate to 2,3-dihydroxyisovalerate, as catalyzed by acetohydroxy acid isomeroreductase; c) 2,3-dihydroxyisovalerate to α-ketoisovalerate, as catalyzed by acetohydroxy acid dehydratase or dihydroxyacid dehydratase; d) α-ketoisovalerate to isobutyraldehyde, as catalyzed by a branched-chain keto acid decarboxylase; and e) isobutyraldehyde to isobutanol, as catalyzed by a branched-chain alcohol dehydrogenase.

Also provided herein are methods for the production of 1-butanol comprising growing a recombinant yeast cell under conditions where 1-butanol is produced and optionally recovering the 1-butanol. Also provided are methods for the production of 2-butanol comprising growing a recombinant yeast cell under conditions where 2-butanol is produced and optionally recovering the 2-butanol. Also provided are methods for the production of isobutanol comprising growing a recombinant yeast cell under conditions where isobutanol is produced and optionally recovering the isobutanol.

Also provided herein are methods for producing a recombinant yeast cell having increased tolerance to butanol comprising:

a) providing a recombinant yeast cell comprising a butanol biosynthetic pathway selected from the group consisting of: i) a 1-butanol biosynthetic pathway; ii) a 2-butanol biosynthetic pathway; and iii) an isobutanol biosynthetic pathway; and b) engineering the yeast cell of (a) to comprise at least one genetic modification which increases activity of the nitrogen starvation-induced filamentous growth response wherein the genetic modification increases MSS11p activity.

Also provided herein are methods for improving fermentative production of butanol, said methods comprise:

a) providing a recombinant yeast cell comprising a butanol biosynthetic pathway selected from the group consisting of:

i) a 1-butanol biosynthetic pathway ii) a 2-butanol biosynthetic pathway; and iii) an isobutanol biosynthetic pathway;

wherein said yeast cell also comprises at least one genetic modification that increases activity of the nitrogen starvation-induced filamentous growth response and increases MSS11p activity; and b) contacting said yeast cell with fermentable sugar whereby said yeast cell produces butanol and said yeast cell has improved tolerance to said butanol as compared to a yeast cell without at least one genetic modification that increases activity of the nitrogen starvation-induced filamentous growth response and MSS11p activity.

BRIEF DESCRIPTION OF THE DRAWINGS AND SEQUENCE DESCRIPTIONS

The various embodiments of the invention can be more fully understood from the following detailed description, the figures, and the accompanying sequence descriptions, which form a part of this application.

Figure 1:
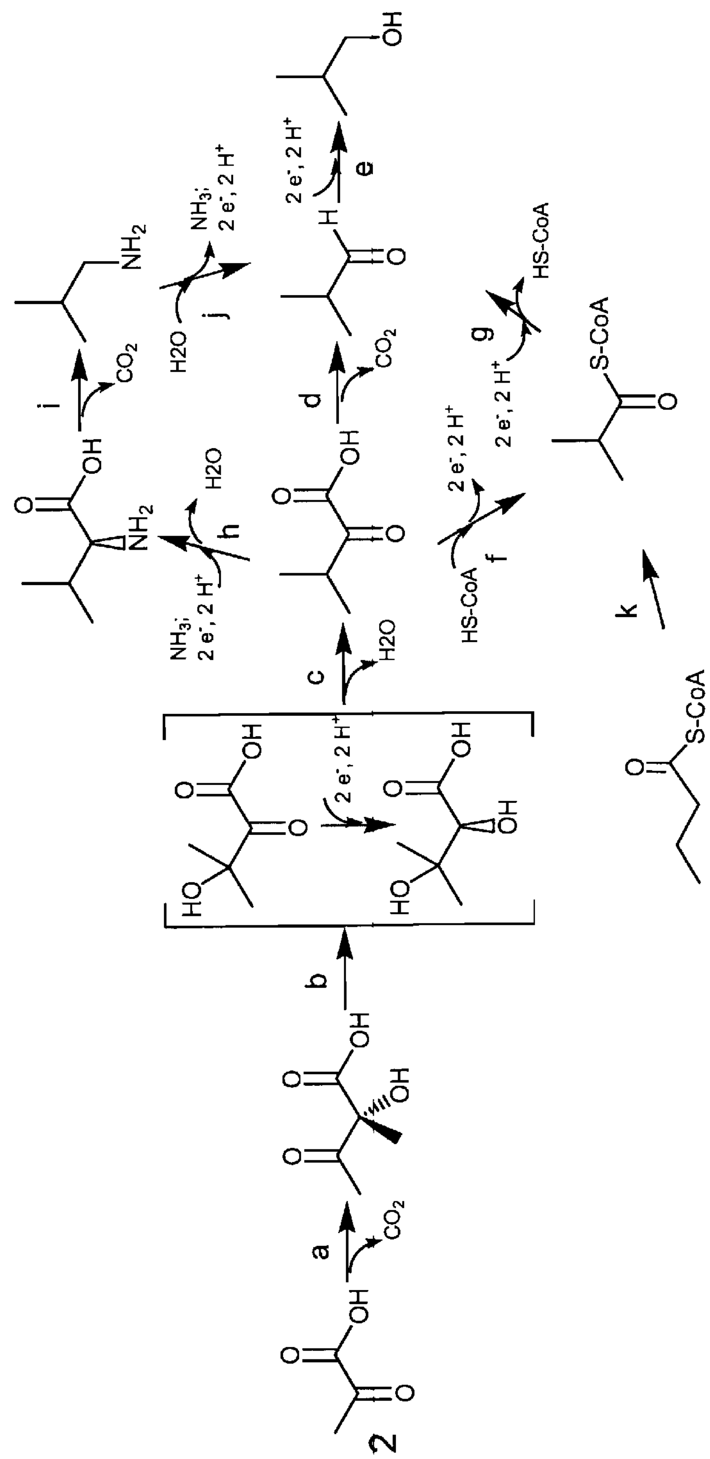
FIG. 1 depicts isobutanol biosynthetic pathways.
Figure 2:
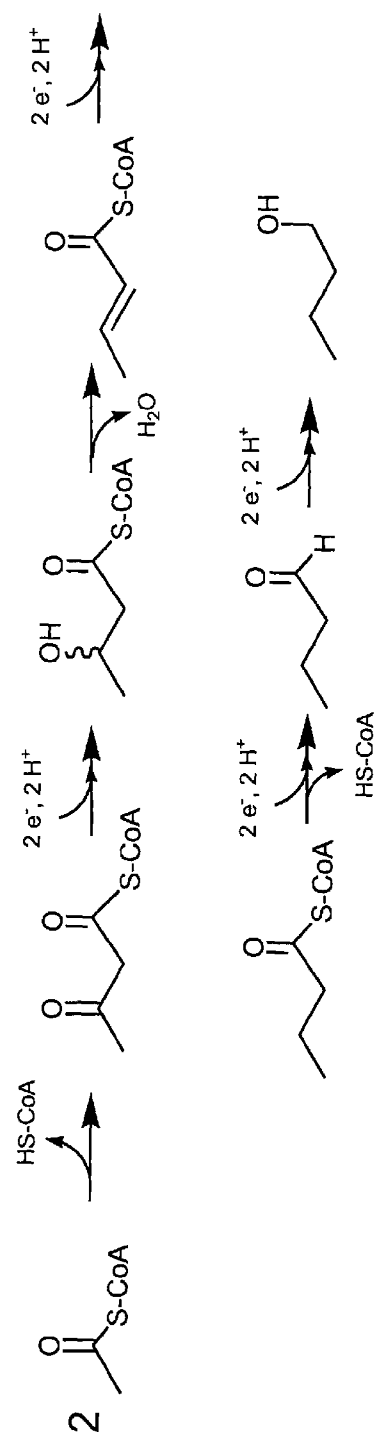
FIG. 2 depicts 1-butanol biosynthetic pathways.
Figure 3:
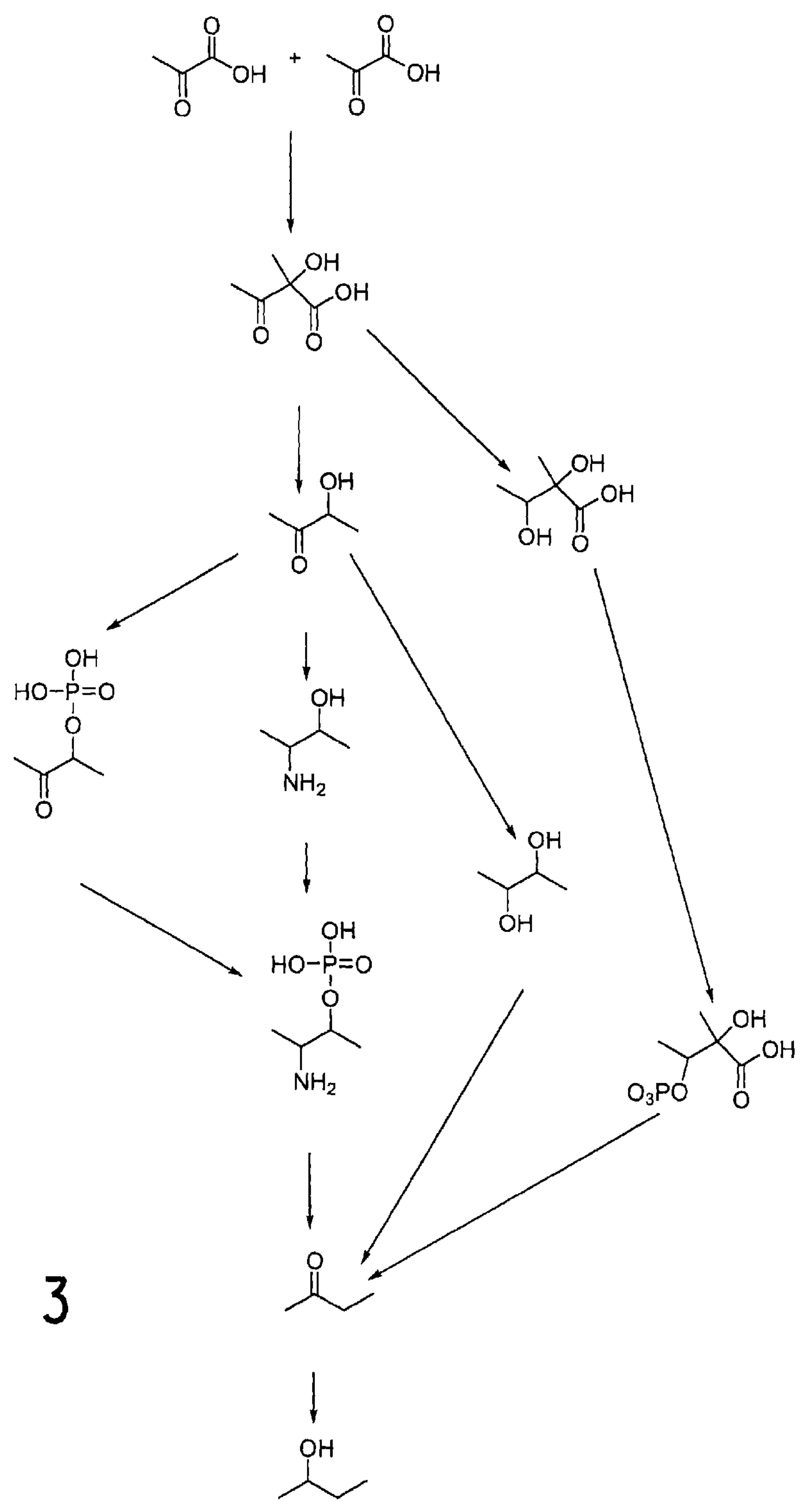
FIG. 3 depicts 2-butanol biosynthetic pathways.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Coding Region and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Coding Region and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus* ruber 219 | 29 | 30 |

TABLE 3

Summary of Coding Region and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase) | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of MSS11 coding region and protein SEQ ID Numbers

| Organism | SEQ ID NO: Nucleic acid | SEQ ID NO: Peptide |
|---|---|---|
| *Saccharomyces cerevisiae* S288C | 49 | 50 |
| *Saccharomyces cerevisiae* RM11-1a | 51 | 52 |
| *Saccharomyces cerevisiae* AWRI1631 | 53 | 54 |

SEQ ID NOs:55 and 56 are primers used for sequencing the ends of the *S. cerevisiae* genomic DNA inserts in the YEp13 vector in identified butanol tolerant clones.

SEQ ID NOs:57 and 58 are primers for PCR amplification of the MSS11 coding sequence SEQ ID NOs:59 and 60 are primers used to screen plasmids by PCR to verify presence of the MSS11 coding region SEQ ID NOs:61 and 62 are primers for PCR of iYDR006C.

SEQ ID NOs:63 and 64 are primers for PCR of iYDR008C.

SEQ ID NOs:65 and 66 are primers for PCR of upTRP1 DR UR.

SEQ ID NOs:67 and 68 are primers for PCR of RA3* DR downTRP1.

SEQ ID NO:69 is the nucleotide sequence of the CUP1 promoter.

SEQ ID NO:70 is the nucleotide sequence of the CYC1 terminator.

SEQ ID NO:71 is the nucleotide sequence of the FBA promoter.

SEQ ID NO:72 is the nucleotide sequence of the ADH1 terminator.

SEQ ID NO:73 is the nucleotide sequence of the GPM promoter.

DETAILED DESCRIPTION

The present invention relates to recombinant yeast cells that are engineered for production of butanol and that additionally are engineered to have increased activity of the nitrogen starvation-induced filamentous growth response. The present yeast cells may have increased expression or activity of at least one protein involved in promoting activity of the nitrogen starvation-induced filamentous growth response including proteins that are receptors of external stimuli, that comprise the TOR (target of rapamycin), cAMP-PKA, filamentous growth MAPK cascade and glucose repression signal pathways, or that are downstream targets of these pathways. These yeast cells have increased tolerance to butanol and may be used for production of butanol which is valuable as a fuel or fuel additive to reduce demand for fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value The term "butanol" as used herein, refers to 1-butanol, 2-butanol, isobutanol, or mixtures thereof.

The terms "butanol tolerant yeast cell" and "tolerant" when used to describe a modified yeast cell of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "mitogen activated protein (MAP) kinase" refers to proteins with EC number EC 2.7.11.24, which are serine/threonine-specific protein kinases that respond to extracellular stimuli (mitogens) and regulate various cellular activities, such as gene expression, mitosis, differentiation, and cell survival/apoptosis.

The term "MSS11" refers to a gene encoding MSS11p which is a transcription factor involved in regulation of invasive growth in response to nutritional signals. The term MSS11p refers herein to any protein that functions similarly to MSS11p in the regulation of invasive growth in response to nutritional signals and that has sequence identity to an MSS11p amino acid sequence that is at least about 55%-60%, 60%-65%, 65%-70%, 70%-75%, 75%-80%, 80-85%, 85%-90%, 90%-95% or 95%-100%.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (Gen Bank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417-484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417-484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "heterologous" or "foreign" gene refers to a gene not normally found in the host organism, but that is introduced into the host organism by gene transfer. Foreign or heterologous genes can comprise native genes inserted into a non-native organism, or chimeric genes. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.,* 215: 403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

As used herein, "substantially similar" enzymes will refer to enzymes belonging to a family of proteins in the art known to share similar structures and function. It is well within the skill of one in the art to identify substantially similar proteins given a known structure. Typical methods to identify substantially similar structures will rely upon known sequence information (nucleotide sequence and/or amino acid sequences) and may include PCR amplification, nucleic acid hybridization, and/or sequence identity/similarity analysis (e.g., sequence alignments between partial and/or complete sequences and/or known functional motifs associated with the desired activity).

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Given the nucleic acid sequences described herein, one of skill in the art can identify substantially similar nucleic acid fragments that may encode proteins having similar activity. Hybridization and washing conditions are well known and exemplified in Sambrook, J., Fritsch, E. F. and Maniatis, T. *Molecular Cloning: A Laboratory Manual,* 3rd ed., Cold Spring Harbor Laboratory: Cold Spring Harbor, N.Y. (2001), particularly Chapter 11 and Table 11.1 therein. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS at 65° C. followed by 0.1×SSC, 0.1% SDS at 65° C., for example.

In one aspect, suitable nucleic acid fragments encode polypeptides that are at least about 70% identical to the amino acid sequences reported herein. In another aspect, the nucleic acid fragments encode amino acid sequences that are about 85-90% identical to the amino acid sequences reported herein. In a further aspect, the nucleic acid fragments encode amino acid sequences that are at least about 90-100% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10), unless otherwise specified. Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "homology" refers to the relationship among sequences whereby there is some extent of likeness, typically due to descent from a common ancestral sequence. Homologous sequences can share homology based on genic, structural, functional and/or behavioral properties. The term "ortholog" or "orthologous sequences" refers herein to a relationship where sequence divergence follows speciation (i.e., homologous sequences in different species arose from a common ancestral gene during speciation). In contrast, the term "paralogous" refers to homologous sequences within a single species that arose by gene duplication. One skilled in the art will be familiar with techniques required to identify homologous, orthologous and paralogous sequences.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein, "default values" will mean any set of values or parameters (as set by the software manufacturer) which originally load with the software when first initialized Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

"Fermentable sugars" refers to a sugar content primarily comprising monosaccharides and some disaccharides that can be used as the carbon source by microorganisms in a fermentation process to produce a target product. Sugars may from any source, including cellulosic, hemicellulosic or ligcellulosic biomass.

Screening for Butanol Tolerance: Involvement of Nitrogen Starvation-Induced Filamentous Growth Response The invention relates to the discovery that increasing activity of the nitrogen starvation-induced filamentous growth response has the effect of increasing tolerance of yeast cells to butanol. The discovery came from screening studies to identify yeast cells containing random fragments of yeast genomic DNA that had increased tolerance to butanol. In these studies, yeast containing a library of random genomic DNA fragments were grown in the presence of isobutanol to identify clones with improved growth relative to controls. In one clone with increased tolerance to butanol the random genomic DNA fragment was found to include the MSS11 gene. A yeast strain with multiple copies of MSS11 had a 2-fold decrease in doubling time over the parental strain in 1.5% (w/v) isobutanol (Example 2 herein).

The MSS11p product of the MSS11 gene is a transcriptional regulator that regulates pseudohyphal differentiation, invasive growth and starch metabolism in response to nutrient availability (Vinod et al. (2008) Mol. Microbiol. 47(1):119-

34). An activation target of MSS11p is the MUC1 gene encoding MUC1p, which is the main cell-surface glycoprotein involved in adhesion-related phenotypes and is essential for filamentous growth in response to nitrogen starvation in *S. cerevisiae* (Reynolds et al. (2001) Science 291:878-881); Lo and Dranginis (1998) Mol. Biol. Cell 9:161-171). Thus increase in MSS11p expression increases activity of the nitrogen starvation-induced filamentous growth response.

Increase in Nitrogen Starvation-Induced Filamentous Growth Response Activity by Directly Engineering MSS11p Expression In the present engineered yeast cell any MSS11p may be expressed in increased amount above the amount found in the cell without MSS11p engineering to provide increased butanol tolerance. In the present yeast cell the endogenous MSS11p of the target yeast cell may be overexpressed, or a heterologous MSS11p may be expressed in the cell to provide increased activity. Examples of MSS11p that may be expressed include those from *Saccharomyces cerevisiae* S288C (coding region SEQ ID NO:49; protein SEQ ID NO:50), *Saccharomyces cerevisiae* RM11-1a (coding region SEQ ID NO:51; protein SEQ ID NO:52), and *Saccharomyces cerevisiae* AWR11631 (coding region SEQ ID NO:53; protein SEQ ID NO:54).

Because the sequences of MSS11 coding regions and the encoded proteins are known, as exemplified in the SEQ ID NOs listed above and given in Table 4, suitable MSS11ps may be readily identified by one skilled in the art on the basis of sequence similarity using bioinformatics approaches. Typically BLAST (described above) searching of publicly available databases with known MSS11p amino acid sequences, such as those provided herein, is used to identify MSS11ps, and their encoding sequences, that may be used in the present strains. These proteins may have at least about 50%-55%, 55%-60%, 60%-65%, 65%-70%, 70%-75%, 75%-80%, 80-85%, 85%-90%, 90%-95% or 95%-99% sequence identity to any of the MSS11ps of SEQ ID NOS:50, 52 or 54 while having MSS11p activity. Identities are based on the Clustal W method of alignment using the default parameters of GAP PENALTY=10, GAP LENGTH PENALTY=0.1, and Gonnet 250 series of protein weight matrix.

In addition to using protein or coding region sequence and bioinformatics methods to identify additional MSS11ps, the sequences described herein or those recited in the art may be used to experimentally identify other homologs in nature. For example each of the MSS11 encoding nucleic acid fragments described herein may be used to isolate genes encoding homologous proteins. Isolation of homologous genes using sequence-dependent protocols is well known in the art. Examples of sequence-dependent protocols include, but are not limited to:

1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the MSS11p encoding genes described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described MSS11p encoding sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Expression of MSS11p is achieved by transforming with a gene comprising a sequence encoding an MSS11p. When using a heterologous coding region, the sequence may be codon-optimized for maximal expression in the target yeast host cell, as well known to one skilled in the art. Methods for gene expression in yeasts are known in the art (see for example *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Expression of genes in yeast typically requires a promoter, operably linked to a coding region of interest, and a transcriptional terminator. A number of yeast promoters can be used in constructing expression cassettes for genes encoding an MSS11p, including, but not limited to constitutive promoters FBA, GPD, ADH1, TEF, and GPM, and the inducible promoters GAL1, GAL10, and CUP1. Suitable transcriptional terminators include, but are not limited to FBAt, GPDt, GPMt, ERG10t, GAL1t, CYC1, and ADH1.

Suitable promoters, transcriptional terminators, and MSS11 coding regions may be cloned into *E. coli*-yeast shuttle vectors, and transformed into yeast cells. These vectors allow propagation in both *E. coli* and yeast strains. Typically the vector contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). Construction of expression vectors with a chimeric gene encoding an MSS11p may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a≥21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y", the promoter-coding regionX-terminator construct is PCR amplified from a plasmid DNA construct and joined to an autotrophic marker (such as URA3) by either SOE PCR or by common restriction digests and cloning. The full cassette, containing the promoter-coding regionX-terminator-URA3 region, is PCR amplified with primer sequences that contain 40-70 bp of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Additional Engineering to Increase Activity of Nitrogen Starvation-Induced Filamentous Growth Response Increased expression of other genes involved in the nitrogen starvation-induced filamentous growth response may be engineered to provide yeast cells of the present invention that have increased tolerance to butanol. Target genes and their encoded proteins for increased expression in the present yeast cells include any gene whose increased expression causes increased activity of the nitrogen starvation-induced filamentous growth response. Target genes may include those that increase activity of MSS11p as well as any gene whose activity is increased by increased activity of MSS11p. The MSS11p transcription factor is involved in regulating invasive growth and starch degradation. MSS11p plays a central role in transcriptional activation of MUC1 (also called FLO11) expression. The MUC1 gene product (MUC1p) is the main cell-surface glycoprotein involved in adhesion-related phenotypes and is essential for filamentous growth in response to nitrogen starvation in *S. cerevisiae* (Reynolds et al. (2001) Science 291:878-881; Lo and Dranginis (1998) Mol. Bio. Cell 9:161-171). Thus increased expression of MUC1p may be engineered to provide increased activity of the nitrogen starvation-induced filamentous growth response, and increased butanol tolerance in the present cells.

MSS11p responds with MUC1 activation to signals transmitted through a network of pathways that includes the TOR (Target Of Rapamycin) pathway, cAMP-PKA pathway, mitogen activated protein kinase (MAPK) module of the nitrogen starvation-induced filamentous growth response, and glucose repression signal pathway. Increased activity of any of these pathways may be engineered to increase MSS11p activity or to in other ways increase the nitrogen starvation-induced filamentous growth response. The TOR pathway responds to nitrogen starvation (Vinod et al. (2008) PLoS ONE 3(2): e1663; Cutler et al. (2001) Mol. Biol. Cell 12:4103-4113). Examples of target genes in this pathway include, but are not limited to, TAP42, SIT4, PHP21, and PNP22. The cAMP-PKA pathway responds to the presence of glucose, sucrose or ammonium ions (Vinod et al. ibid.; Verstrepen and Klis (2006) Mol. Microbiol. 60:5-15). Examples of target genes in this pathway include, but are not limited to, MEP2, GPR1, GPB1, GPB2, CYR1, BCY1, RAS, TPK1, TPK2, SFL1, HDA1, and FLOG. The MAPK module of the nitrogen starvation-induced filamentous growth response responds to nitrogen starvation and other uncharacterized signals (Vinod et al. ibid.; Verstrepen and Klis ibid.). Examples of target genes in this pathway include, but are not limited to, MEP2, STE11, STE7, KSS1, STE12, TEC1, MSB2, CDC42, SHO1, STE20, IRA1, and IRA2. The glucose repression pathway responds to glucose (Verstrepen and Klis ibid.). Examples of target genes in this pathway include, but are not limited to, SNF1, SNF4, SIP1, TUP1, SSN6, MIG1, and NRG1.

The activity of any of these proteins may be increased by overexpressing the endogenous encoding sequence in a yeast cell or by expressing a heterologous sequence encoding the protein. Expression of any of these proteins may be accomplished as described above for MSS11p. The coding sequences and encoded proteins that may be used in the present cells may be readily identified in publicly available databases by one skilled in the art.

Host Yeast Cells

The target genes and proteins that are engineered to provide an increase in CWI pathway activity to confer butanol tolerance may be engineered in any yeast cell that is additionally engineered for production of butanol. Suitable yeasts include, but are not limited to, *Saccharomyces, Schizosaccharomyces, Hansenula, Candida, Kluyveromyces, Yarrowia, Issatchenkia* and *Pichia*. Suitable strains include, but are not limited to, *Saccharomyces cerevisiae Schizosaccharomyces pombe, Kluyveromyces lactis, Kluyveromyces thermotolerans, Candida glabrata, Candida albicans, Pichia stipitis* and *Yarrowia lipolytica.*

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other. The butanol biosynthetic pathway may be a 1-butanol, 2-butanol, or isobutanol biosynthetic pathway.

Suitable biosynthetic pathways are known in the art, and certain suitable pathways are described herein. In some embodiments, the butanol biosynthetic pathway comprises at least one gene that is heterologous to the yeast cell. In some embodiments, genes encoding proteins which catalyze each substrate to product conversion of the butanol biosynthetic pathway are heterologous to the yeast cell. In some embodiments, the butanol biosynthetic pathway comprises more than one gene that is heterologous to the yeast cell. In some embodiments, genes encoding proteins which catalyze each substrate to product conversion of the butanol biosynthetic pathway are heterologous to the yeast cell. In some embodiments, the yeast cell comprises heterologous genes encoding the proteins for each substrate to product conversion of a butanol biosynthetic pathway.

Likewise, certain suitable proteins having the ability to catalyze the indicated substrate to product conversions are described herein and other suitable proteins are described in the art. For example, US Published Patent Application Nos. US20080261230 and US20090163376, incorporated herein by reference, describe acetohydroxy acid isomeroreductases; U.S. patent application Ser. No. 12/569,636, incorporated by reference, describes suitable dihydroxyacid dehydratases; a suitable alcohol dehydrogenase is described in US Published Patent Application US20090269823, incorporated herein by reference.

1-Butanol Biosynthetic Pathway

A suitable biosynthetic pathway for the production of 1-butanol that may be used is described by Donaldson et al. in U.S. Patent Application Publication No. US20080182308A1, incorporated herein by reference. This biosynthetic pathway comprises the following substrate to product conversions:

a) acetyl-CoA to acetoacetyl-CoA, as catalyzed for example by acetyl-CoA acetyltransferase with protein sequence such as SEQ ID NO:2, 4 or 40 (which may be encoded, for example, by the genes given as SEQ ID NO:1, 3 or 39);

b) acetoacetyl-CoA to 3-hydroxybutyryl-CoA, as catalyzed for example by 3-hydroxybutyryl-CoA dehydrogenase with protein sequence such as SEQ ID NO:6 (which may be encoded, for example, by the gene given as SEQ ID NO:5);

c) 3-hydroxybutyryl-CoA to crotonyl-CoA, as catalyzed for example by crotonase with protein sequence such as SEQ ID NO:8 (which may be encoded, for example, by the gene given as SEQ ID NO:7);

d) crotonyl-CoA to butyryl-CoA, as catalyzed for example by butyryl-CoA dehydrogenase with protein sequence such as SEQ ID NO:10 (which may be encoded, for example, by the gene given as SEQ ID NO:9);

e) butyryl-CoA to butyraldehyde, as catalyzed for example by butyraldehyde dehydrogenase with protein sequence such as SEQ ID NO:12 (which may be encoded, for example, by the gene given as SEQ ID NO:11); and f) butyraldehyde to 1-butanol, as catalyzed for example by 1-butanol dehydrogenase with protein sequence such as SEQ ID NO:14 or 16 (which may be encoded, for example, by the genes given as SEQ ID NO:13 or 15).

The pathway requires no ATP and generates $NAD^+$ and/or $NADP^+$, thus, it balances with the central, metabolic routes that generate acetyl-CoA.

Other suitable biosynthetic pathways for the production of 1-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 1-butanol biosynthetic pathway comprising a sequence that has at least about 70%-75%, 75%-80%, 80-85%, 85%-90%, 90%-95% or 95%-99% sequence identity to a 1-butanol pathway protein provided herein.

2-Butanol Biosynthetic Pathway

Suitable biosynthetic pathways for the production of 2-butanol that may be used are described by Donaldson et al. in U.S. Patent Application Publication Nos. US20070259410A1 and US 20070292927A1, each incorporated herein by reference. One 2-butanol biosynthetic pathway comprises the following substrate to product conversions:

a) pyruvate to alpha-acetolactate, as catalyzed for example by acetolactate synthase with protein sequence such as SEQ ID NO:20 (which may be encoded, for example, by the gene given as SEQ ID NO:19);

b) alpha-acetolactate to acetoin, as catalyzed for example by acetolactate decarboxylase with protein sequence such as SEQ ID NO:18 (which may be encoded, for example, by the gene given as SEQ ID NO:17);

c) acetoin to 2,3-butanediol, as catalyzed for example by butanediol dehydrogenase with protein sequence such as SEQ ID NO:22 (which may be encoded, for example, by the gene given as SEQ ID NO:21);

d) 2,3-butanediol to 2-butanone, catalyzed for example by butanediol dehydratase with protein sequence such as SEQ ID NO:24, 26, or 28 (which may be encoded, for example, by genes given as SEQ ID NO:23, 25, or 27); and e) 2-butanone to 2-butanol, as catalyzed for example by 2-butanol dehydrogenase with protein sequence such as SEQ ID NO:30 (which may be encoded, for example, by the gene given as SEQ ID NO:29).

Other suitable biosynthetic pathways for the production of 2-butanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express a 2-butanol biosynthetic pathway comprising a sequence that has at least about 70%-75%, 75%-80%, 80-85%, 85%-90%, 90%-95% or 95%-99% sequence identity to a 2-butanol pathway protein provided herein.

Isobutanol Biosynthetic Pathway

Suitable biosynthetic pathways for the production of isobutanol that may be used are described by Maggio-Hall et al. in U.S. Patent Application Publication No. US20070092957 A1, incorporated herein by reference. One isobutanol biosynthetic pathway comprises the following substrate to product conversions:

a) pyruvate to acetolactate, as catalyzed for example by acetolactate synthase with protein sequence such as SEQ ID NO:20 or 42 (which may be encoded, for example, by genes given as SEQ ID NO:19 or 41);

b) acetolactate to 2,3-dihydroxyisovalerate, as catalyzed for example by acetohydroxy acid isomeroreductase with protein sequence such as SEQ ID NO:32, 44 or 46 (which may be encoded, for example, by genes given as SEQ ID NO:31, 43 or 45);

c) 2,3-dihydroxyisovalerate to α-ketoisovalerate, as catalyzed for example by acetohydroxy acid dehydratase with protein sequence such as SEQ ID NO:34 (which may be encoded, for example, by the gene given as SEQ ID NO:33); or dihydroxyacid dehydratase with protein sequence such as SEQ ID NO:48 (which may be encoded, for example, by the gene given as SEQ ID NO:47);

d) α-ketoisovalerate to isobutyraldehyde, as catalyzed for example by a branched-chain keto acid decarboxylase with protein sequence such as SEQ ID NO:36 (which may be encoded, for example, by the gene given as SEQ ID NO:35); and e) isobutyraldehyde to isobutanol, as catalyzed for example by a branched-chain alcohol dehydrogenase with protein sequence such as SEQ ID NO:38 (which may be encoded, for example, by the gene given as SEQ ID NO:37).

Other suitable biosynthetic pathways for the production of isobutanol will be apparent to those of skill in the art. It will be appreciated that yeast cells may be engineered to express proteins that retain the ability to catalyze the indicated substrate to product conversion but have less than 100% sequence identity to the protein sequences provided herein. In one embodiment, yeast cells may be engineered to express an isobutanol biosynthetic pathway comprising a sequence that has at least about 70%-75%, 75%-80%, 80-85%, 85%-90%, 90%-95% or 95%-99% sequence identity to an isobutanol pathway protein provided herein.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48. Methods for gene expression in yeasts that may be used for butanol pathway genes are described above for expression of MSS11p.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1-Compd.*, [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Industrial Batch and Continuous Fermentations

The present process may employ a batch method of fermentation. A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as CO2. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.,* 36:227, (1992), herein incorporated by reference.

Although the present invention is performed in batch mode it is contemplated that the method would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1-butanol production.

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent. Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures and yeast cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989) or in *Yeast Protocols, Second Edition* (Wei Xiao, ed; Humana Press, Totowa, N.J. (2006))). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Methods for Determining Isobutanol Concentration in Culture Media

The concentration of isobutanol in the culture media can be determined by a number of methods known in the art. For example, a specific high performance liquid chromatography (HPLC) method utilizes a Shodex SH-1011 column with a Shodex SH-G guard column, both purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions described. Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 22° C. for 5 min; and FID detection is employed at 240° C. with 26 mL/min helium makeup gas. The retention time of isobutanol is 4.5 min.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "μM" means micromolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography.

CM refers to synthetic complete medium which is described in Amberg, Burke and Strathern, 2005, Methods in Yeast Genetics, Cold Spring Harbor Laboratory Press, Cold Spring Harbor, N.Y.

Example 1

Isolation of a Plasmid from a Yeast Genomic DNA Library that Includes MSS11 and Causes Increased Isobutanol Tolerance A *S. cerevisiae* genomic library in the multicopy *E. coli*/yeast shuttle vector YEp13 (ATCC 37323; Reed et al. (1989)

*J. Cell. Sci. Suppl.* 12:29-37) was obtained from the American Type Culture Collection (Manassas, Va.). The library was provided in an *E. coli* host and supplies complete coverage of the *S. cerevisiae* genome with 10,000 clones containing random and/or overlapping fragments of genomic DNA. The library was amplified by growth of the *E. coli* host in LB for 16 hours with ampicillin (50 μg/ml) at 37° C. with shaking. The genomic library was extracted from *E. coli* using a Qiaprep Spin Miniprep Kit (Cat. No. 27104) and transformed into *S. cerevisiae* strain BY4741 (ATCC 201388) using a lithium acetate transformation procedure (Gietz et al. (1995) *Yeast* 11:355-360).

Competing chemostat bioreactors were used to identify components of the yeast genomic library that enhance the isobutanol tolerance of *S. cerevisiae*. Two Appilikon fermentors (Appilikon Inc., Clinton, N.J.) were operated as anoxic chemostat bioreactors. Each bioreactor system was composed of a 1 liter dished bottom reactor, Controller ADI 1032 P100, and stirrer unit with marine and turbine impellers. Bio Controller ADI 1030 Z510300020 with appropriate sensors monitored pH, dissolved oxygen, and temperature. A Cole Parmer pump and pump head were used for addition of acid and base to maintain pH 6.8. The temperature was held at 30° C. by using a circulating water bath. Both chemostats contained 250 ml of yeast synthetic dropout medium (YSDM: 6.7 g/L yeast nitrogen base without amino acids (Sigma-Aldrich, Inc., St. Louis, Mo., cat. # Y0626-250G), 1.6 g/L amino acid dropout mix without leucine (Sigma-Aldrich, Inc., St. Louis, Mo., cat. # Y1376-20G), 20 g/L glucose and 0.5% (w/v) isobutanol. Cellular growth in the chemostats was measured by determining optical density of the cultures at 600 nm ($OD_{600}$) according to standard methods. A pool of at least 10,000 *S. cerevisiae* BY4741 transformants containing the genomic library was inoculated into one of the chemostats (CSTR A). A second identical chemostat (CSTR B) was inoculated with BY4741 containing YEp13 as a control. The chemostats were initially operated in batch mode (dilution rate=0.0 $hr^{-1}$) for 24 hours, and then new culture medium was pumped into both chemostats from the same reservoir. The $OD_{600}$ decreased to less than 0.1 in both chemostats at flow rates of 0.75 ml/min (dilution rate=0.18 $hr^{-1}$) and 0.5 ml/min (dilution rate=0.12 $hr^{-1}$) and then increased to >2.0 when the flow rate was reduced to 0.0 ml/min. The yeast population in CSTR A was then maintained at $OD_{600}$>1.0 at flow rates 0.2 to 0.3 ml/min whereas the control yeast population in CSTR B rapidly decreased to $OD_{600}$<0.02 with the same flow rates. Hence, chemostat CSTR A contained a population of *S. cerevisiae* transformants that tolerated at least 0.5% isobutanol.

Isobutanol tolerant strains of yeast were isolated from CSTR A by plating a sample of cells from Day 9 onto YSDM agar with 0.5% isobutanol. The plates were incubated at 30° C. for 72 hours. Representative colonies (180) were inoculated from the agar medium into 150 μl of YSDM medium with 0.5% isobutanol into the wells of covered U-bottom microtiter plates (BD Diagnostic Systems; Catalog No. 353077).

The Bioscreen C automated growth curve system (Growth Curves USA, Piscataway, N.J.)) was used to test the isobutanol tolerance of 30 randomly chosen isolates. The growth experiments were conducted in YSDM medium with 0.0%, 1.0% or 1.5% isobutanol. The doubling times for each isolate in each isobutanol concentration were determined from the linear portions of the corresponding growth curves. A total of 23 isolates grew better than control strain BY4741(YEp13) in the presence of isobutanol. Plasmid DNA was obtained from 19 out of the 23 yeast isolates and transformed into *E. coli* according to standard procedures. Plasmid was isolated and both ends of the genomic DNA fragment in each plasmid from duplicate *E. coli* transformants were sequenced using primers specific for YEp13 (ype13-fwd: 5'-CTATGCGCACCCGTTCTCGGAGC SEQ ID NO:55, or ype13-rev: 5'-CGCTCATGAGCCCGAAGTGGCG SEQ ID NO:56) and standard methods. All genomic fragment end sequences obtained from all 19 plasmids were aligned in both directions using the Clustal W algorithm in Align X from Vector NTI (Invitrogen). The results of this analysis indicated that the same fragment was present in multiple isolates that were designated PNY0008, PNY0012 and PNY0023.

The genomic library plasmid in the PNY0008 isolate was designated as pYGL0008. Plasmid pYGL0008 was transferred from PNY0008 to *E. coli*, isolated from *E. coli* and again transformed into BY4741. In Bioscreen C growth experiments, the resulting transformant PNY0008A1 had a faster doubling time (630 minutes) than BY4741(YEp13) (1283 minutes) when grown in 1.5% isobutanol. Hence, the isobutanol tolerance of isolate PNY0008 was attributed to yeast genomic library plasmid pYGL0008.

Figure 4:
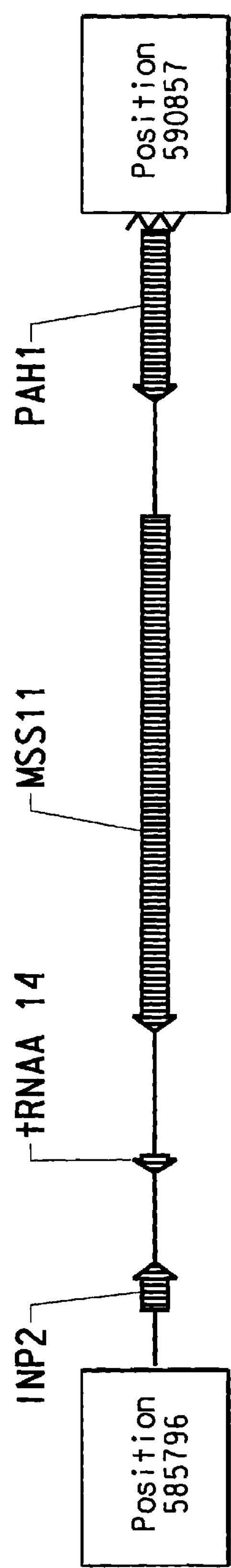
FIG. 4 shows a diagram of the *S. cerevisiae* genomic DNA fragment present in the pYGL0008 plasmid.

The results of a BLAST search indicated that the end sequences obtained from the pYGL0008 genomic DNA insert corresponded to a yeast genomic fragment of 5,061 bp that extends from position 585796 to position 590857 on *S. cerevisiae* chromosome XIII (FIG. 4). The pYGL0008 genomic fragment contains three complete open reading frames (ORFs) and a portion of the PAH1 ORF. The first complete ORF is INP2 which encodes a peroxisome-specific receptor that is important for peroxisome inheritance (Fagarasanu et al. (2006) Biochimica et Biophysica Acta (BBA)—Molecular Cell Research 1763:1669-1677). The second complete ORF is tRNA14 which encodes a valine-specific tRNA (Bowman et al. (1997) Nature 387(6632 Suppl):90-93). The third complete ORF is MSS11 which is a transcriptional regulator that regulates starch degradation and pseudohyphal growth (Gagiano et al. (1999) Molecular Microbiology 31:103-116).

Example 2 (Prophetic)

Overexpression of MSS11 in *S. cerevisiae* for the Purpose of Increasing Isobutanol Tolerance The purpose of this prophetic example is to describe how to increase isobutanol tolerance in a yeast strain by constructing a recombinant plasmid that enables overexpression of MSS11. The MSS11 gene is amplified by PCR and inserted into a suitable yeast expression plasmid. The expression plasmid is a low copy number (CEN/ARS) or a high copy number (2μ) plasmid with a yeast transcription promoter (such as CYC1 promoter, ADH promoter, TEF promoter or GPD promoter), a yeast transcription terminator and a selectable marker (such as URA3, LEU2, TRP1 or HIS3). Several suitable expression plasmids such as p426TEF (with a URA3 selection marker) have been described (Mumberg et al. (1995) Gene 156:119-22).

The MSS11 coding sequence is amplified by PCR from *S. cerevisiae* genomic DNA with primers forMSS (5'-GGTATCTCCCGGATCCTTTGTC-3': SEQ ID NO:57) and revMSS (5'-CGGTTAGTATTGGAAGAATTCCGATGAAACACT-3': SEQ ID NO:58) according to standard methods. The forMSS primer will add a BamH1 restriction site to the 5' end of MSS11. The revMSS primer will add an EcoR1 restriction site to the 3' end of MSS11. The MSS11 PCR product is cut with restriction nucleases BamH1 and EcoR1 and ligated to expression plasmid p426TEF that has been cut with the same restriction nucleases. In the resulting clone is a chimeric gene including the TEF promoter, MSS11 coding region, and CYC1 terminator. The ligated DNA is transformed into *E. coli* with selection for ampicillin resistance using standard methods. Transformants are screened by PCR using primers profor1 (5'-AAGGAGTACTTGTTTTTAGAATATACGGTCAACG-3': SEQ ID NO:59) and termrev2 (5'-GATGGAATATGAGGGACCATTTGTGGGTTG-3': SEQ ID NO:60) to verify presence of plasmids with the MSS11 coding region. The plasmid containing MSS11 (p426TEF::MSS11) is then recovered from *E. coli* using a Qiaprep Spin Miniprep Kit (Cat. No. 27104). Plasmid p426TEF::MSS11 is transformed into *S. cerevisiae* strain BY4743 using a standard lithium acetate transformation procedure (Gietz et al. (1995) *Yeast* 11:355-360; *Methods in Yeast Genetics,* 2005, Cold Spring Harbor Laboratory Press, Cold Spring Harbor, N.Y., pp. 201-202) with selection on synthetic complete medium lacking uracil at 30° C. The transformants have increased isobutanol tolerance as shown by growth experiments in medium containing isobutanol as described in Example 1.

Example 3 (Prophetic)

Production of Isobutanol in Recombinant *S. cerevisiae* With Engineered Isobutanol Pathway and MSS11 Overexpression The purpose of this prophetic example is to describe how to enhance isobutanol production in a yeast strain by combining an isobutanol biosynthetic pathway with MSS11 overexpression. To this end we need to disrupt TRP1, the gene encoding phosphoribosylanthranilate isomerase that catalyzes the third step in tryptophan biosynthesis, to provide a third selectable marker. BY4741 is the starting strain. A cassette containing DNA sequences that are located upstream and downstream just outside of TRP1 (up TRP1 and downTRP1) is created containing the following elements: upTRP1 DR URA3* DR downTRP1, where DR are direct repeat sequences and URA3* is a heterologous URA3 gene. The upTRP1 DR URA3* DR downTRP1 fragment is constructed by the method of Reid et al. ((2002) Yeast 19(4):319-328). Following this method the 5' and 3' flanking regions of the TRP1 gene, which contain the up TRP1 and downTRP1 sequences, are prepared. These are called intergenic DNAs iYHR029C and iYHR030C, respectively.

Intergenic DNA iYDR006C is amplified from *S. cerevisiae* genomic DNA using PCR with the following primers where the small letters are the adaptamers described in Reid et al. (ibid) and the capital letters are yeast genomic DNA:

```
Forward:
                                  (SEQ ID NO: 61)
ccgctgctaggcgcgccgtgTCTGAAAACGGAAGAGGAGTAGG

Reverse:
                                  (SEQ ID NO: 62)
gcagggatgcggccgctgacATAACAGACATACTCCAAGCTGCC
```

Intergenic DNA iYDR008C is amplified from *S. cerevisiae* genomic DNA using PCR with the following primers where the small letters are the adaptamers described in Reid et al. (ibid.) and the capital letters are yeast genomic DNA:

```
Forward:
                                  (SEQ ID NO: 63)
ccgctgctaggcgcgccgtgCATTTGGCTTTTTGATTGATTGTAC
```

-continued

```
Reverse:
                                  (SEQ ID NO: 64)
gcagggatgcggccgctgacACTTTTATTTTCTCTTTTTGCACTCCT
```

The two intergenic DNA PCR fragments are each used together with the plasmid pWJ1077, containing DR URA3*DR (Reid et al. ibid.), as template for PCR to produce DNA fragments containing each intergenic DNA sequence and a portion of the URA3* sequence, with overlap of the URA3* sequence between the two resulting fragments: upTRP1 DR UR and RA3* DR downTRP1. This is because there is complementarity between the right end of iYDR006C and a sequence on the plasmid pWJ1077 left of the DR upstream relative to URA3. Similarly, there is complementarity between the left end of iYDR006C and a sequence on the plasmid pWJ1077 right of the DR downstream relative to URA3. Primers for iYDR006C and pWJ1077 templates are C and kli3' (SEQ ID NOS:65 and 66). Primers for iYDR008C and pWJ1077 templates are D and kli5" (SEQ ID NOs:67 and 68).

Co-transformation of these two fragments into yeast allows recombination between the two fragments to create a cassette containing an intact URA3* gene flanked by upTRP1 and downTRP1 sequences. Recombination of this cassette into the yeast chromosome results in the replacement of TRP1 by DR URA3* DR. Transformants with this recombination event are selected by demanding growth in the absence of pyrimidines but in the presence of tryptophan. The recombinant requires tryptophan to grow. Excision of URA3* is accomplished by homologous recombination between the DR's and its loss is selected for with 5-FOA to create BY4741ΔTRP1.

Construction of vectors pRS423::CUP1p-alsS+FBAp-ILV3 and pHR81::FBAp-ILV5-GPMp-kivD is described in US Patent Publication # US20070092957 A1, Example 17, which is herein incorporated by reference. pRS423::CUP1p-alsS+FBAp-ILV3 has a chimeric gene containing the CUP1 promoter (SEQ ID NO:69), the alsS coding region from *Bacillus subtilis* (SEQ ID NO:41), and CYC1 terminator (SEQ ID NO:70) as well as a chimeric gene containing the FBA promoter (SEQ ID NO:71), the coding region of the ILV3 gene of *S. cerevisiae* (SEQ ID NO:47), and the ADH1 terminator (SEQ ID NO:72). pHR81::FBAp-ILV5+GPMp-kivD is the pHR81 vector (ATCC #87541) with a chimeric gene containing the FBA promoter, the coding region of the ILV5 gene of *S. cerevisiae* (SEQ ID NO:43), and the CYC1 terminator as well as a chimeric gene containing the GPM promoter (SEQ ID NO:73), the coding region from kivD gene of *Lactococcus* lactis (SEQ ID NO:35), and the ADH1 terminator. pHR81 has URA3 and leu2-d selection markers.

Plasmid vectors pRS423::CUP1p-alsS+FBAp-ILV3 and pHR81::FBAp-ILV5+GPMp-kivD are transformed into BY4741ΔTRP1 using standard genetic techniques to yield the doubly transformed strain BY4741ΔTRP1-iso (*Methods in Yeast Genetics,* 2005, Cold Spring Harbor Laboratory Press, Cold Spring Harbor, N.Y.). BY4741ΔTRP1-iso is maintained on synthetic complete media lacking histidine and uracil.

Next, p424 (Mumberg et al. (1995) Gene 156:119-22; ATCC catalog #87357) is used to clone and express MSS11 as described in Example 2 to obtain the plasmid p424-MSS11. The same chimeric gene is present in p424-MSS11 as in p426TEF::MSS11, but the vector uses a TRP1 selection marker for yeast. The plasmid is then isolated from *E. coli* and transformed into the yeast strains selecting for the ability to grow in the absence of tryptophan (TRP1 function).

BY4741ΔTRP1-iso is transformed with p424TEF-MSS11 selecting for the ability to grow without tryptophan supplementation yielding BY4741ΔTRP1-iso-MSS11. BY4741ΔTRP1-iso is also transformed with p424 selecting for the ability to grow without tryptophan supplementation yielding BY4741ΔTRP1-iso-c.

Aerobic cultures are grown in 250 ml flasks containing 50 ml synthetic complete media lacking histidine, tryptophan and uracil, and supplemented with 2% glucose in an Innova4000 incubator (New Brunswick Scientific, Edison, N.J.) at 30° C. and 225 rpm. Low oxygen cultures are prepared by adding 45 mL of medium to 60 mL serum vials that are sealed with crimped caps after inoculation and kept at 30° C. Approximately 24 h and 48 h after induction with 0.03 mM $CuSO_4$ (final concentration), an aliquot of the broth is analyzed by HPLC (Shodex Sugar SH1011 column (Showa Denko America, Inc. NY) with refractive index (RI) detection and GC(HP-Innowax, 0.32 mm×0.25 μm×30 m (Agilent Technologies, Inc., Santa Clara, Calif.) with flame ionization detection (FID) for isobutanol content. Isobutanol is detected. More isobutanol is produced by BY4741ΔTRP1-iso-MSS11 than by BY4741ΔTRP1-iso-c.

What is claimed is:

1. A recombinant yeast cell comprising:

(a) an isobutanol biosynthetic pathway, wherein the recombinant yeast cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:

(i) pyruvate to acetolactate catalyzed by the acetolactate synthase, (ii) acetolactate to 2,3-dihydroxyisovalerate catalyzed by the acetohydroxy acid isomeroreductase, (iii) 2,3-dihydroxyisovalerate to α-ketoisovalerate catalyzed by the acetohydroxy acid dehydratase or dihydroxyacid dehydratase, (iv) α-ketoisovalerate to isobutyraldehyde catalyzed by the branched-chain keto acid decarboxylase, and (v) isobutyraldehyde to isobutanol catalyzed by the branched-chain alcohol dehydrogenase; and (b) at least one genetic modification which increases activity of the nitrogen starvation-induced filamentous growth response, wherein the genetic modification is heterologous expression of a transcription factor involved in regulation of invasive growth in response to nutritional signals, wherein the transcription factor has at least 95% sequence identity to the *Saccharomyces cerevisiae* MSS11 protein of SEQ ID NO: 50, SEQ ID NO: 52, or SEQ ID NO: 54; wherein the yeast cell has an increase in tolerance to isobutanol as compared with the corresponding yeast cell that lacks the at least one genetic modification of (b).

2. The recombinant yeast cell of claim 1 selected from the group consisting of *Saccharomyces, Schizosaccharomyces, Hansenula, Candida, Kluyveromyces, Yarrowia* and *Pichia*.

3. A recombinant yeast cell comprising:

(a) an isobutanol biosynthetic pathway, wherein the recombinant yeast cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:

(i) pyruvate to acetolactate catalyzed by the acetolactate synthase, (ii) acetolactate to 2,3-dihydroxyisovalerate catalyzed by the acetohydroxy acid isomeroreductase, (iii) 2,3-dihydroxyisovalerate to α-ketoisovalerate catalyzed by the acetohydroxy acid dehydratase or dihydroxyacid dehydratase, (iv) α-ketoisovalerate to isobutyraldehyde catalyzed by the branched-chain keto acid decarboxylase, and (v) isobutyraldehyde to isobutanol catalyzed by the branched-chain alcohol dehydrogenase; and (b) at least one heterologous transcription factor involved in regulation of invasive growth in response to nutritional signals, wherein the transcription factor has at least 95% sequence identity to the *Saccharomyces cerevisiae* MSS11 protein of SEQ ID NO: 50, SEQ ID NO: 52, or SEQ ID NO: 54.

4. A method for the production of isobutanol comprising growing a recombinant yeast cell under conditions where isobutanol is produced, wherein said recombinant yeast cell comprises:

(a) an isobutanol biosynthetic pathway, wherein the recombinant yeast cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:

(i) pyruvate to acetolactate catalyzed by the acetolactate synthase, (ii) acetolactate to 2,3-dihydroxyisovalerate catalyzed by the acetohydroxy acid isomeroreductase, (iii) 2,3-dihydroxyisovalerate to α-ketoisovalerate catalyzed by the acetohydroxy acid dehydratase or dihydroxyacid dehydratase, (iv) α-ketoisovalerate to isobutyraldehyde catalyzed by the branched-chain keto acid decarboxylase, and (v) isobutyraldehyde to isobutanol catalyzed by the branched-chain alcohol dehydrogenase; and (b) at least one genetic modification which increases activity of the nitrogen starvation-induced filamentous growth response, wherein the genetic modification is heterologous expression of a transcription factor involved in regulation of invasive growth in response to nutritional signals, wherein the transcription factor has at least 95% sequence identity to the *Saccharomyces cerevisiae* MSS11 protein of SEQ ID NO: 50, SEQ ID NO: 52, or SEQ ID NO: 54; wherein the yeast cell has an increase in tolerance to isobutanol as compared with the corresponding yeast cell that lacks the at least one genetic modification of (b).

5. A method for improving fermentative production of isobutanol comprising:

(I) providing a recombinant yeast cell which comprises:

(a) an isobutanol biosynthetic pathway, wherein the recombinant yeast cell comprises heterologous genes encoding an acetolactate synthase, an acetohydroxy acid isomeroreductase, an acetohydroxy acid dehydratase or dihydroxyacid dehydratase, a branched-chain keto acid decarboxylase, and a branched-chain alcohol dehydrogenase that perform the following substrate to product conversions:

(i) pyruvate to acetolactate catalyzed by the acetolactate synthase, (ii) acetolactate to 2,3-dihydroxyisovalerate catalyzed by the acetohydroxy acid isomeroreductase, (iii) 2,3-dihydroxyisovalerate to α-ketoisovalerate catalyzed by the acetohydroxy acid dehydratase or dihydroxyacid dehydratase, (iv) α-ketoisovalerate to isobutyraldehyde catalyzed by the branched-chain keto acid decarboxylase, and (v) isobutyraldehyde to isobutanol catalyzed by the branched-chain alcohol dehydrogenase; and (b) at least one genetic modification which increases activity of the nitrogen starvation-induced filamentous growth response, wherein the genetic modification is heterologous expression of a transcription factor involved in regulation of invasive growth in response to nutritional signals, wherein the transcription factor has at least 95% sequence identity to the *Saccharomyces cerevisiae* MSS11 protein of SEQ ID NO: 50, SEQ ID NO: 52, or SEQ ID NO: 54; wherein the yeast cell has an increase in tolerance to isobutanol as compared with the corresponding yeast cell that lacks the at least one genetic modification of (b); and (II) contacting said yeast cell with fermentable sugar whereby said yeast cell produces isobutanol and wherein the fermentative production of isobutanol is improved.

6. The method of claim 4, further comprising recovering the isobutanol.

* * * * *